United States Patent
Chen et al.

(10) Patent No.: US 10,675,346 B2
(45) Date of Patent: Jun. 9, 2020

(54) ANTIGENIC POLYPEPTIDES COMPRISING PRE-HAIRPIN INTERMEDIATE CONFORMATIONS OF HIV-1 GP41

(75) Inventors: Bing Chen, Westwood, MA (US); Gary H. Frey, Nashua, NH (US); Jia Chen, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 379 days.

(21) Appl. No.: 13/884,823

(22) PCT Filed: Nov. 9, 2011

(86) PCT No.: PCT/US2011/059915
§ 371 (c)(1),
(2), (4) Date: Jan. 8, 2014

(87) PCT Pub. No.: WO2012/064816
PCT Pub. Date: May 18, 2012

(65) Prior Publication Data
US 2014/0112936 A1 Apr. 24, 2014

Related U.S. Application Data

(60) Provisional application No. 61/413,055, filed on Nov. 12, 2010.

(51) Int. Cl.
| A61K 39/21 | (2006.01) |
| C07K 14/005 | (2006.01) |
| G01N 33/569 | (2006.01) |
| A61K 39/00 | (2006.01) |

(52) U.S. Cl.
CPC ............ *A61K 39/21* (2013.01); *C07K 14/005* (2013.01); *G01N 33/56988* (2013.01); *A61K 39/00* (2013.01); *C07K 2319/73* (2013.01); *C12N 2740/16033* (2013.01); *C12N 2740/16122* (2013.01); *C12N 2740/16134* (2013.01); *G01N 2333/162* (2013.01)

(58) Field of Classification Search
CPC .. A61K 39/21; C07K 2319/73; C07K 14/005; C12N 2740/16122; C12N 2740/16134
See application file for complete search history.

(56) References Cited

U.S. PATENT DOCUMENTS

2005/0089526 A1  4/2005  Moore et al.

FOREIGN PATENT DOCUMENTS

| WO | WO-2009111304 A2 | 9/2009 |
| WO | WO 2009/111304 A2 * | 11/2009 |

OTHER PUBLICATIONS

TheiBen, G., 2002, Secret life of genes, Nature 415:741.*
Fitch, W. M., 2000, Homology: a personal view on some of the problems, Trends in Genetics 16(5):227-231.*
Sen, J., et al., 2010, Alanine scanning mutagenesis of HIV-1 gp41 heptad repeat region 1: insight into the gp120-gp41 interaction, Biochem. 49:5057-5065.*
Gallo, R. C., 2005, The end or the beginning of the drive to an HIV-preventive vaccine: a view from over 20 years, The Lancet 366:1894-1898.*
Barouch, D. H., 2008, Challenges in the development of an HIV-1 vaccine, Nature 455:613-619.*
West, Jr., A. P., et al., 2014, Structural insights on the role of antibodies in HIV-1 vaccine and therapy, Cell 156:633-648.*
Desrosiers, R. C., Mar. 2004, Prospects for an AIDS vaccine, Nat. Med. 10(3):221-223.*
Gallo, R. C., Nov. 2005, The end or the beginning of the drive to an HIV-preventive vaccine: a view from over 20 years, The Lancet, 366:1894-1898.*
Haynes, B. F., and D. C. Montefiori, Jun. 2006, Aiming to induce broadly reactive neutralizing antibody responses with HIV-1 vaccine candidates, Expert Rev. Vaccines 5(3):347-363.*
Lewis, G. K., et al., Nov. 2014, Antibody persistence and T-cell balance: Two key factors confronting HIV vaccine development, PNAS 111(44):15614-15621.*
Miller, et al., "A Human Monoclonal Antibody Neutralizes Diverse HIV-1 Isolates by Binding a Critical gp41 Epitope", Proc. Natl Acad Sci USA 2005, 102(41):14759-14764.
Young, Lee W., "International Search Report", World Intellectual Property Organization, Patent Cooperation Treaty, May 18, 2012, 5 pages.

* cited by examiner

*Primary Examiner* — Jeffrey S Parkin
(74) *Attorney, Agent, or Firm* — Mintz Levin Cohn Ferris Glovsky and Popeo, P.C.; Peter F. Corless; Nicholas A. Zachariades

(57) ABSTRACT

Isolated, antigenic polypeptides including a pre-hairpin intermediate conformation of gp41 and vectors encoding such polypeptides are provided. Exemplary pre-hairpin intermediate conformations of gp41 include an oligomerization domain; a heptad repeat 2 motif; and a membrane-proximal external region, where the polypeptide lacks a heptad repeat 1 motif, and where the isolated, antigenic polypeptides elicit production of a broadly neutralizing antibody against HIV when injected into a subject. Antibodies that bind to a pre-hairpin intermediate conformation of gp41 and methods of making antibodies a that bind to pre-hairpin intermediate conformation of gp41 are also provided. Vaccines against a pre-hairpin intermediate conformation of gp41, as well as methods of treating subjects infected with HIV, preventing HIV infection, and inhibiting HIV-mediated activities are also provided. Methods of screening compounds that bind to an isolated, pre-hairpin intermediate conformation of gp41 are further provided.

20 Claims, 22 Drawing Sheets
Specification includes a Sequence Listing.

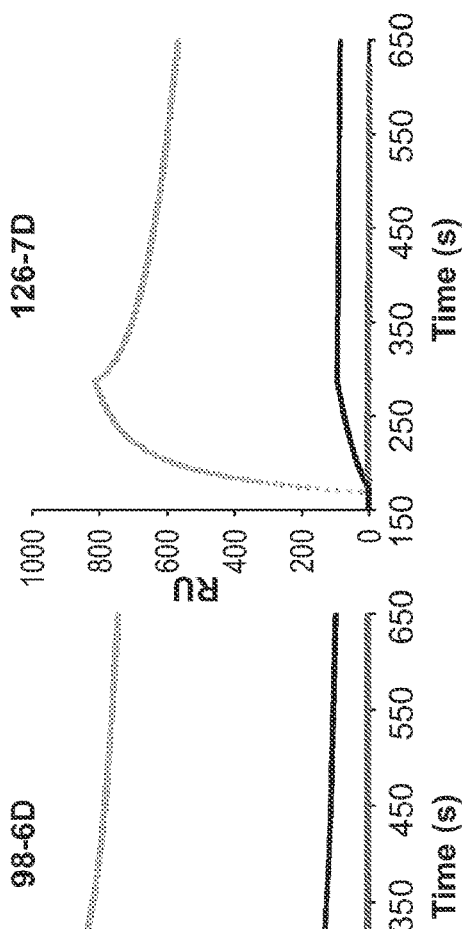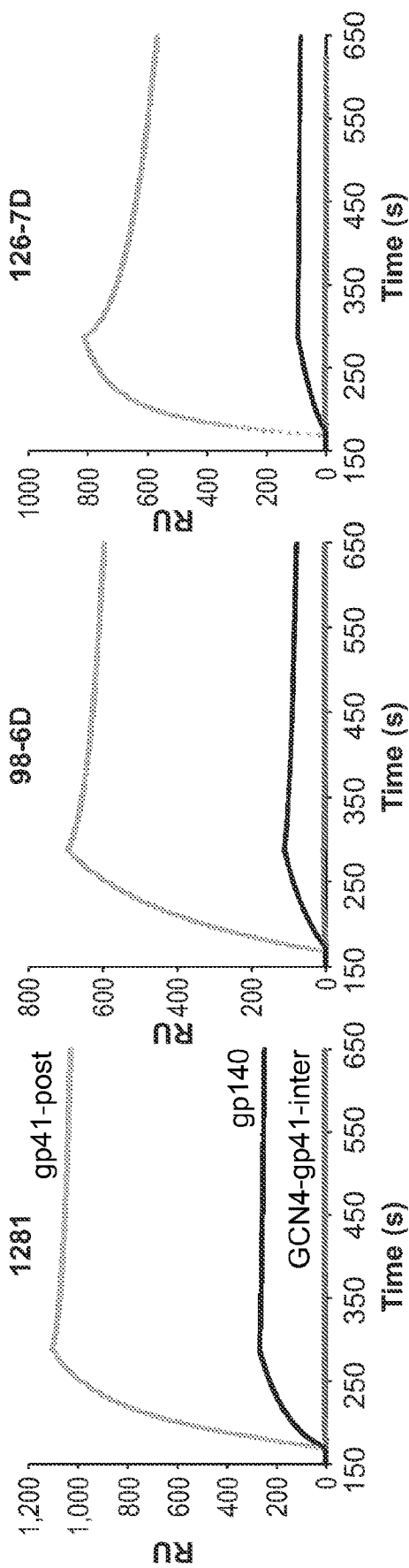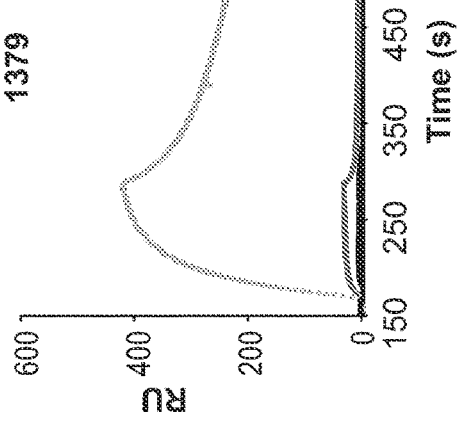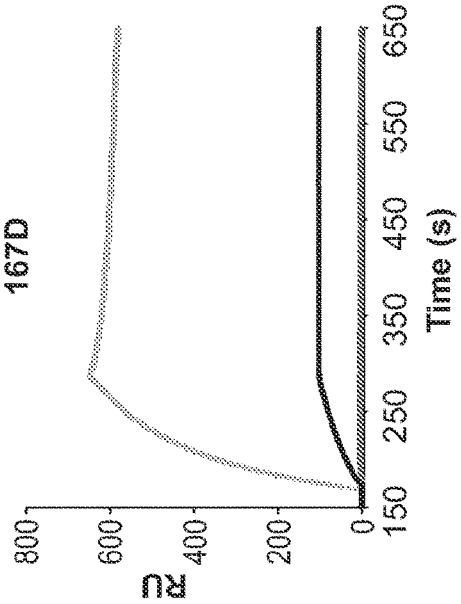
FIG. 2a  FIG. 2b  FIG. 2c  FIG. 2d  FIG. 2e

| FIG. 9-1 | FIG. 9-3 |
| --- | --- |
| FIG. 9-2 | FIG. 9-4 |

US 10,675,346 B2

ANTIGENIC POLYPEPTIDES COMPRISING PRE-HAIRPIN INTERMEDIATE CONFORMATIONS OF HIV-1 GP41

RELATED APPLICATION DATA

This application is a national stage application of PCT/US2011/059915, filed Nov. 9, 2011, which claims the benefit of U.S. Provisional Patent Application No. 61/413,055, filed Nov. 12, 2010 and are hereby incorporated herein by reference in their entirety for all purposes.

STATEMENT OF GOVERNMENT INTERESTS

This invention was made with government support under Grant Nos. AI084794 and GM083680, awarded by The National Institutes of Health. The Government has certain rights in the invention.

FIELD

The present invention relates to methods and compositions for neutralizing viral infection, for example, infection by HIV (e.g., HIV-1).

BACKGROUND

The first critical step of HIV-1 infection is fusion of viral and target cell membranes. Viral attachment and membrane fusion are mediated by the viral envelope glycoprotein upon engagement with cellular receptors (Harrison (2008) *Nat. Struct. Mol. Biol.* 15:690; Wyatt and Sodroski (1998) *Science* 280:1884). The envelope protein is synthesized as a precursor, gp160, which trimerizes and undergoes cleavage into two, non-covalently-associated fragments: the receptor-binding fragment gp120 and the fusion fragment gp41 (Allan et al. (1985) *Science* 228:1091; Veronese et al. (1985) *Science* 229:1402). Three copies of each fragment make up the mature viral spike, which constitutes the sole antigen on the virion surface. Sequential binding of gp120 to the primary receptor CD4 and co-receptor (e.g. CCR5 and CXCR4) induces large conformational changes which then trigger dissociation of gp120 and a cascade of refolding events in gp41 (Harrison, Supra; Harrison (2005) *Advances in Virus Research* 64:231). Gp41, with its C-terminal trans-membrane segment inserted in the viral membrane, is folded into a pre-fusion conformation within the precursor, gp160. Cleavage between gp120 and gp41 makes this pre-fusion conformation metastable with respect to a rearranged, post-fusion conformation. When triggered by the binding of gp120 to the co-receptor, the N-terminal fusion peptide of gp41 translocates and inserts into the target cell membrane. The extended conformation of the protein, with the fusion peptide inserted into cell membrane and the transmembrane anchor in the viral membrane, is referred to as the "pre-hairpin intermediate" (Chan and Kim (1998) *Cell* 93:681). The pre-hairpin intermediate can be targeted by T-20/Enfuvirtide, the first approved fusion-inhibiting antiviral drug, as well as by certain broadly neutralizing antibodies (Kilby and Eron (2003) *New Engl. J. Med.* 348:2228; Wild (1992) *Proc. Natl. Acad. Sci. USA* 89:10537; Frey et al. (2008) *Proc. Natl. Acad. Sci. USA* 105:3739). Subsequent rearrangements involve folding back of the C-terminal heptad repeat 2 (HR2) region of gp41 into a hairpin conformation, creating a six-helix bundle, which places the fusion peptide and the transmembrane segment at the same end of the molecule (Chan et al. (1997) *Cell* 89:263; Weissenhorn et al. (1997) *Nature* 387:426). This irreversible refolding of gp41 effectively brings the two membranes together. During the fusion process, gp41 exhibits at least three distinct conformational states: the pre-fusion conformation, an extended, pre-hairpin intermediate, and the post-fusion conformation.

HIV-1 infected patients typically generate strong antibody responses to the envelope glycoprotein, but most of these antibodies are either non-neutralizing or strain-specific, and many recognize epitopes occluded on mature trimeric spikes or epitopes located in the highly variable loops. Extensive glycosylation, sequence diversity, and receptor-triggered conformational changes and epitope masking pose great challenges to generation of broadly reactive neutralizing antibodies (NAbs) (Richman et al. (2003) *Proc. Natl. Acad. Sci. USA* 100:4144; Kwong et al. (2002) *Nature* 420:678; Wei et al. (2003) *Nature* 422:307). Some patient sera show broadly neutralizing activity, but immunogens that can induce such antibody responses have remained elusive (Stamatatos et al. (2009) *Nat. Med.* 15:866). Nevertheless, a number of broadly reactive neutralizing monoclonal antibodies (mAb) have been isolated that recognize regions of the HIV-1 envelope glycoprotein. Some are located on gp120: the CD4 binding site (CD4bs), the V2 and V3 loops and the carbohydrates on the outer domain of gp120 (Wu et al. (2010) *Science* 329:856; Zhou et al. (2010) *Science* 329:811; Walker et al. (2009) *Science* 326:285; Trkola et al. (1996) *J. Virol.* 70:1100; Burton et al. (1994) *Science* 266:1024; Hioe et al. (2010) *PLoS One* 5:e10254; Zolla-Pazner and Cardozo (2010) *Nat. Rev. Immunol.* 10:527). Additional neutralizing antibodies target regions on gp41 adjacent to the viral membrane and are called the membrane proximal external region (MPER; residues 662-683 (HXB2 numbering)) (Stiegler et al. (2001) *AIDS Res. Hum. Retroviruses* 17:1757; Muster et al. (1993) *J. Virol.* 67:6642; Zwick et al. (2001) *J. Virol.* 75:10892).

Gp41 also induces non-neutralizing antibodies which are much more abundant in patients than neutralizing ones. The non-neutralizing antibodies have been classified into two groups based on the location of their epitopes. Cluster I antibodies react with the immunodominant C-C loop of gp41 (residues 590-600), and cluster II antibodies recognize another immunodominant segment (residues 644-663) next to the MPER (Xu et al. (1991) *J. Virol.* 65:4832). Members in the latter group can bind HIV-1 gp41 with high affinity, but have weak or no neutralizing or antiviral activities (Hioe et al. (1997) *Int. Immunol.* 9:1281; Holl et al. (2006) *J. Virol.* 80:6177). The prototype of this group includes mAbs 98-6, 126-6, 167-D, 1281 and 1379, isolated by immortalizing plasma B cells from HIV-1 positive patients (Xu et al., Supra; Gorny et al. (1989) *Proc. Natl. Acad. Sci. USA* 86:1624; Gorny et al. (2000) *Virology* 267:220; Pinter et al. (1989) *J. Virol.* 63:2674). As the conformation of these envelope preparations has not been fully assessed, it remains uncertain which conformation(s) of gp41 the cluster II mAbs recognize and why they are incapable of blocking HIV-1 infection, as do the MPER-directed neutralizing antibodies.

SUMMARY

The present invention is directed in part on the discovery of the structural basis for the drastic differences between MPER-directed antibodies and cluster II antibodies in their ability to neutralize HIV-1 infection. Improved gp41 polypeptides are provided that mimic the HIV-1 pre-hairpin intermediate conformation. One such polypeptide binds tightly to broadly neutralizing antibodies 2F5, 4E10 and Z13e1.

It has been discovered by biochemical and structural means that anti-HIV-1 gp41 cluster II antibodies show high binding affinity for the post-fusion conformation of gp41, and do not bind or bind only weakly to the stable, homogeneous gp41 preparations representing the pre-hairpin intermediate or the pre-fusion conformation. Without intending to be bound by scientific theory, these antibodies are non-neutralizing because they target a late step in the viral entry process, when membrane fusion is likely to be complete. The non-neutralizing antibodies may be induced in HIV-1 infected patients by gp41 antigens in a triggered, post-fusion form, and may accordingly serve as irrelevant decoys to distract the immune system and to contribute to production of ineffective humoral responses. Strategies based on the results disclosed herein are provided to guide rational design of HIV-1 gp41-based vaccines.

Accordingly, in certain exemplary embodiments, an isolated, antigenic polypeptide comprising a pre-hairpin intermediate conformation of gp41 is provided. The polypeptide includes an oligomerization domain, a heptad repeat 2 motif, and a membrane-proximal external region, and the polypeptide lacks a heptad repeat 1 motif. The polypeptide can elicit production of a broadly neutralizing antibody against HIV when injected into a subject. In certain aspects, the polypeptide includes a C-C loop domain. In certain aspects, the oligomerization domain is a coiled coil domain. In other aspects, the polypeptide substantially fails to elicit production of weak or non-neutralizing antibodies (e.g., cluster II antibodies) when injected into a subject.

In certain exemplary embodiments, an isolated, antigenic polypeptide comprising a pre-hairpin intermediate conformation of gp41 including an oligomerization domain, a heptad repeat 2 motif, and a membrane-proximal external region is provided, wherein the polypeptide elicits production of a broadly neutralizing antibody and substantially fails to elicit production of cluster II antibodies against HIV when injected into a subject.

In certain exemplary embodiments, an isolated, antigenic polypeptide comprising a pre-hairpin intermediate conformation of gp41 including an oligomerization domain, a heptad repeat 2 motif, and a membrane-proximal external region is provided, wherein the polypeptide lacks a post-fusion conformation of gp41 comprising a heptad repeat 1 motif and a heptad repeat 2 motif arranged as a bundle, and wherein the polypeptide elicits production of a broadly neutralizing antibody against HIV when injected into a subject.

In certain exemplary embodiments, an isolated, antigenic polypeptide comprising a pre-hairpin intermediate conformation of gp41 is provided having the following order, an oligomerization domain at the amino terminus of the polypeptide, a C-C loop domain carboxy terminal to the oligomerization domain, a heptad repeat 2 motif carboxy terminal to the C-C loop, and a membrane-proximal external region at the carboxy terminus of the polypeptide. In certain aspects, the polypeptide elicits production of a broadly neutralizing antibody when injected into a subject. In other aspects, the polypeptide substantially fails to elicit production of weak or non-neutralizing antibodies (e.g., cluster II antibodies) when injected into a subject.

In certain exemplary embodiments, a vector expressing a polynucleotide encoding a polypeptide comprising a pre-hairpin intermediate conformation of gp41 is provided. The vector expresses a polypeptide having an oligomerization domain, a heptad repeat 2 motif, and a membrane-proximal external region. The polypeptide substantially fails to elicit production of cluster II antibodies against HIV when injected into a subject. In certain aspects, the polypeptide lacks a heptad repeat 1 motif.

In certain exemplary embodiments, a method of therapeutically treating a subject infected with HIV is provided. The method includes contacting a subject infected with HIV with an isolated polypeptide comprising a pre-hairpin intermediate conformation of gp41 including an oligomerization domain, a heptad repeat 2 motif, and a membrane-proximal external region, and lacking a heptad repeat 1 domain, and eliciting an immune response in the subject to therapeutically treat the subject. In certain aspects, gp41 is expressed in a single (e.g., antigenic) conformation in the subject. In other aspects, a broadly neutralizing antibody is produced in the subject. In still other aspects, the polypeptide substantially fails to elicit production of weak or non-neutralizing antibodies (e.g., cluster II antibodies) in the subject. In certain aspects, the HIV titer in the subject infected with HIV is decreased. In other aspects, the HIV is HIV-1. In yet other aspects, HIV infection is eliminated from the HIV-infected subject.

In certain exemplary embodiments, a method of inhibiting an HIV-mediated activity in a subject in need thereof is provided. The method includes contacting an HIV-infected subject with a polypeptide comprising an isolated, pre-hairpin intermediate conformation of an envelope glycoprotein including an oligomerization domain, a heptad repeat 2 motif, and a membrane-proximal external region, and lacking a heptad repeat 1 motif, and inhibiting an HIV-mediated activity. In certain aspects, the HIV-mediated activity is viral spread. In other aspects, HIV titer in the HIV-infected subject is decreased.

In certain exemplary embodiments, a method of preventing HIV infection in a subject including contacting a subject with an isolated polypeptide comprising a pre-hairpin intermediate conformation of an envelope glycoprotein including an oligomerization domain, a heptad repeat 2 motif, and a membrane-proximal external region, and lacking a heptad repeat 1 motif, and eliciting an immune response against the polypeptide in the subject is provided. In certain aspects, a broadly neutralizing antibody against HIV is raised in the subject. In other aspects, the polypeptide substantially fails to elicit production of weak or non-neutralizing antibodies (e.g., cluster II antibodies) in the subject.

In certain exemplary embodiments, a method of screening a compound that binds to an isolated, pre-hairpin intermediate conformation of gp41 including providing an isolated polypeptide including an oligomerization domain, a heptad repeat 2 motif, and a membrane-proximal external region, and lacking a heptad repeat 1 motif, contacting the polypeptide with the compound, and determining the ability of the compound to bind to the polypeptide is provided. In certain aspects, the compound inhibits an HIV-mediated activity. In other aspects, the compound is provided in a library.

In certain exemplary embodiments, a vaccine having an epitope comprising an isolated, pre-hairpin intermediate conformation of gp41 including an oligomerization domain, a heptad repeat 2 motif, and a membrane-proximal external region, and lacking a heptad repeat 1 motif is provided.

In certain exemplary embodiments, an anti-gp41 antibody specific against an epitope comprising an isolated, pre-hairpin intermediate conformation of gp41 including an oligomerization domain, a heptad repeat 2 motif, and a membrane-proximal external region, and lacking a heptad repeat 1 motif is provided.

In certain exemplary embodiments, a method of making an anti-gp41 antibody comprising the steps of providing a subject, contacting the subject with an epitope comprising an isolated, pre-hairpin intermediate conformation of gp41 including an oligomerization domain, a heptad repeat 2 motif, and a membrane-proximal external region, and lacking a heptad repeat 1 motif, and allowing production of an anti-gp41 antibody in the subject is provided. In certain aspects, polyclonal antibodies are isolated from the subject. In other aspects, a lymphocyte is isolated from the subject, and, optionally, a monoclonal antibody is made from the lymphocyte. In other aspects, the polypeptide substantially fails to elicit production of weak or non-neutralizing antibodies (e.g., cluster II antibodies) in the subject.

In certain exemplary embodiments, an isolated polypeptide having at least 75%, 80%, 85%, 90%, 95%, 96%, 97%, 98%, 99% or more sequence homology to SEQ ID NO:1 is provided.

In certain exemplary embodiments, a vector expressing a nucleic acid sequence encoding a polypeptide having at least 75%, 80%, 85%, 90%, 95%, 96%, 97%, 98%, 99% or more sequence homology to SEQ ID NO:1 is provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which.

The recorded sensorgrams are in black and the fits in green. A single curve is shown for 4E10 binding, as the chip could not be completely regenerated. All injections were carried out in duplicate and gave essentially identical results. Only one of the duplicates is shown. Binding constants for each interaction were summarized in Table 1.

FIGS. 8A-8E graphically depict SPR analysis of interactions between anti-HIV-1 gp41 cluster II antibodies and gp140, GCN4-gp41-inter and gp41-post. Similar to FIG. 2, cluster II mAbs 1281, 98-6D, 126-7D, 167D and 1379 were analyzed by a surface plasmon resonance (SPR) assay for binding to HIV-1 gp140, GCN4-gp41-inter and gp41-post. To avoid potential artifacts introduced by protein immobilization, Protein A was first immobilized on a CM5 chip surface and used to capture the antibodies. Each of gp140, GCN4-gp41-inter or gp41-post at 50 nM was passed over each antibody surface individually. The recorded sensorgrams for gp41-post are in red, gp140 in black and GCN4-gp41-inter in blue. Antibody tested is as indicated. The molecular mass of gp140 is ~520 kDa; GCN4-gp41-inter is 56 kDa and gp41-post is 33 kDa. Since the SPR response is proportional to the molecular mass of binding analyte, the differences between gp41-post (red) and gp140 (black) are indeed much greater than those shown in the figure.

Figure 8A:
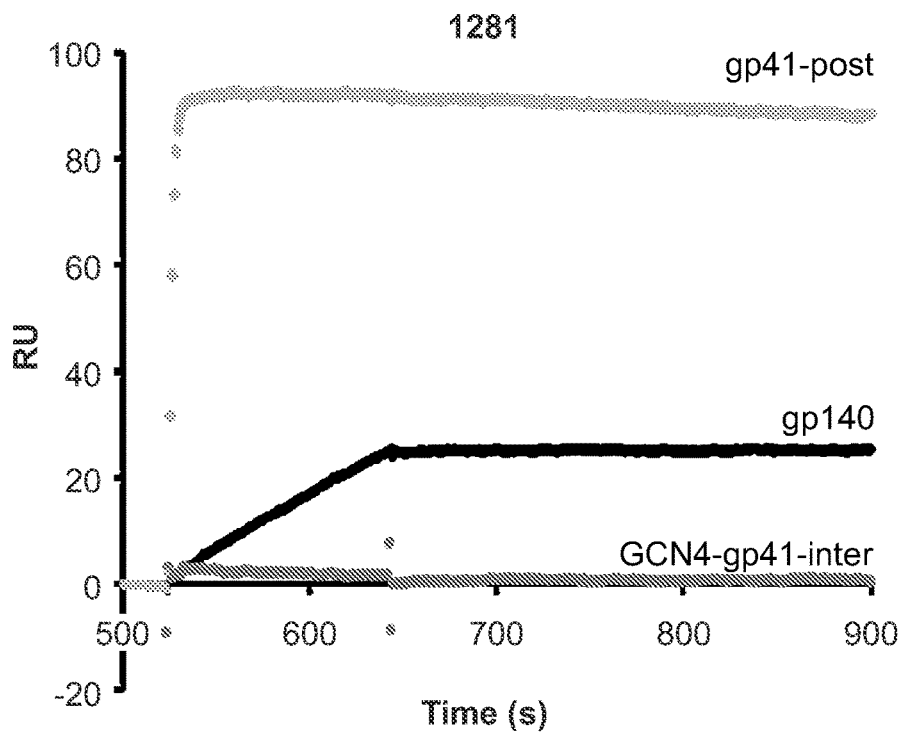
Figure 8B:
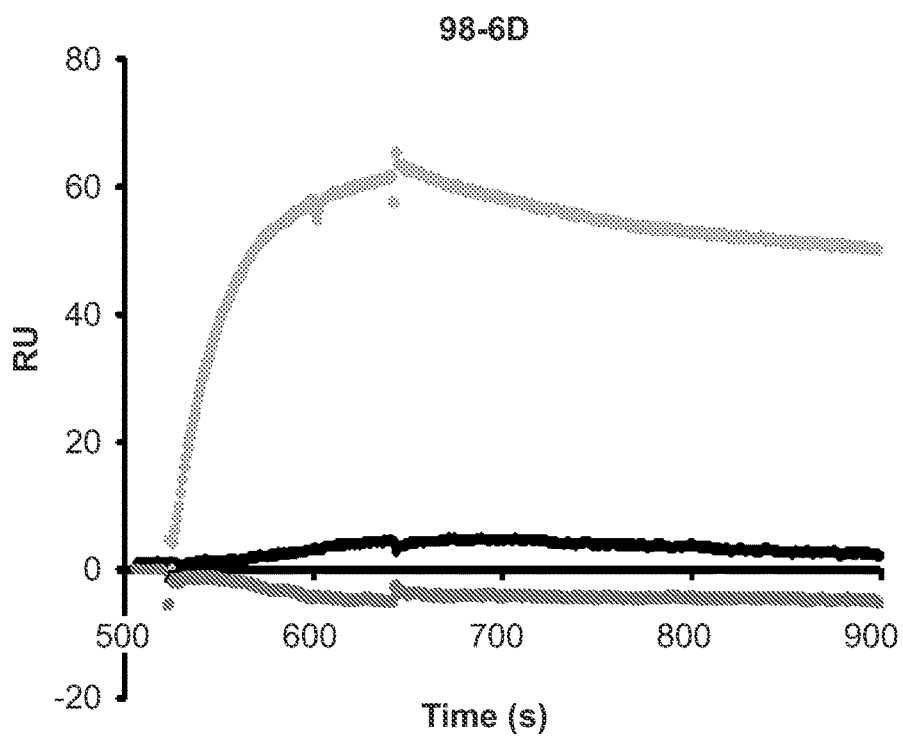
Figure 8C:
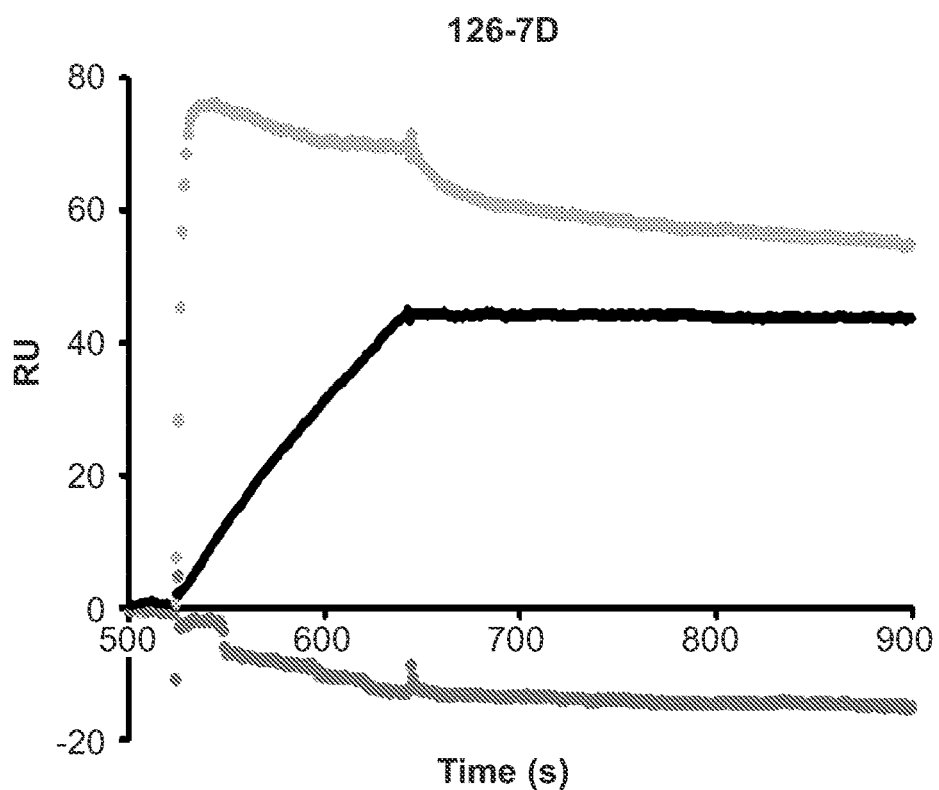
Figure 8D:
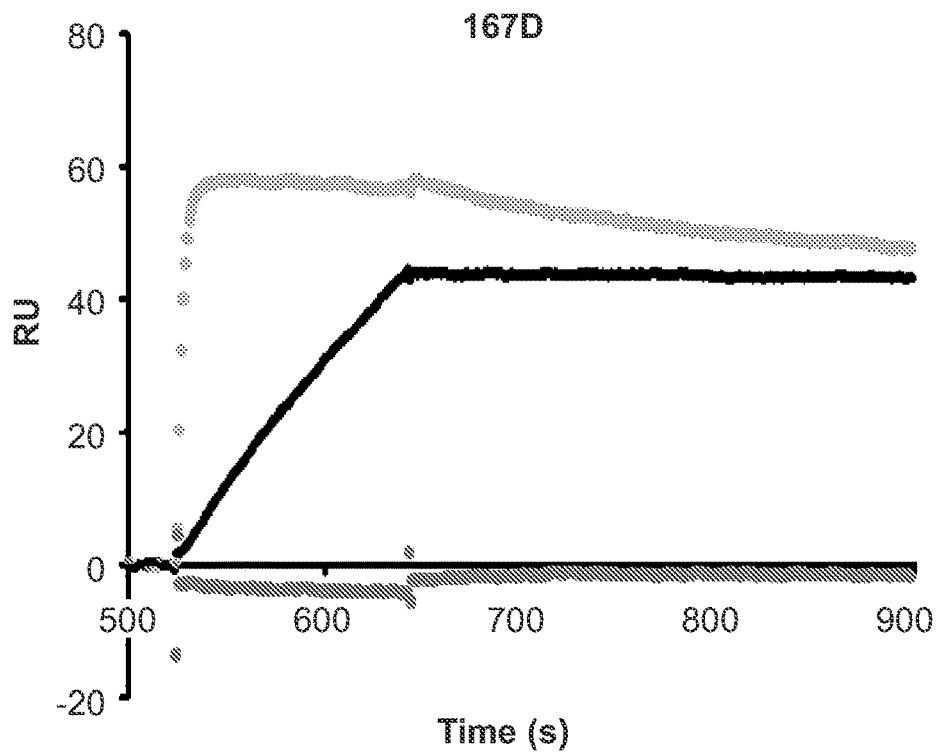
Figures 8E, 9:
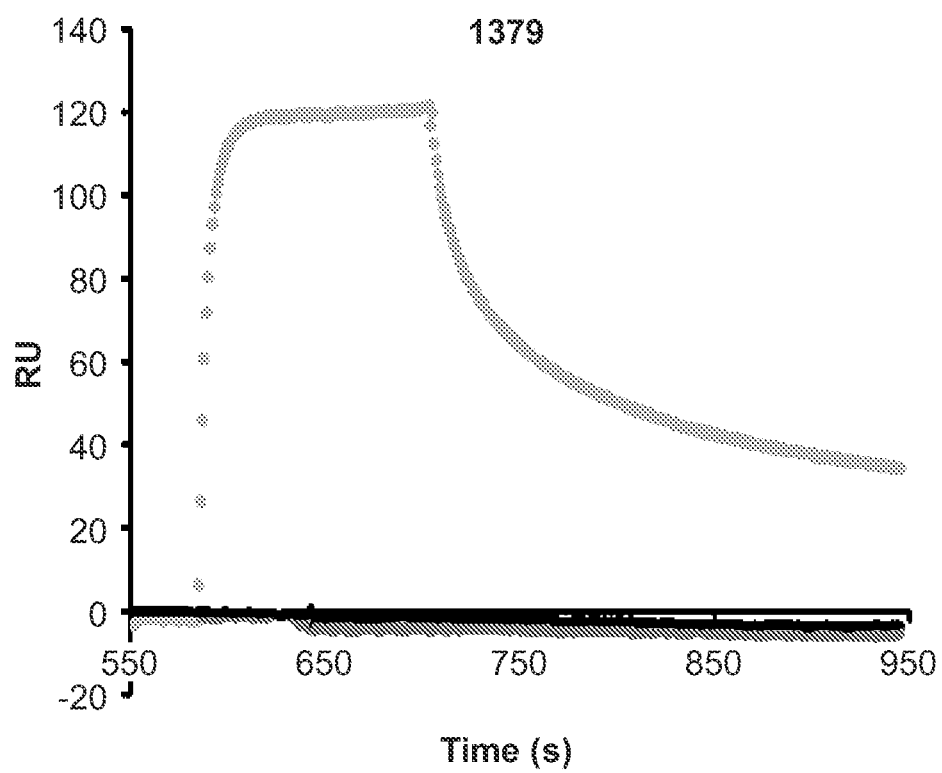

FIG. 9 graphically depicts antibody binding to the HIV-1 92UG037.8 envelope trimer expressed on 293T cell surfaces. 293T cells were transfected with either 92UG037.8 gp160, or no DNA as a negative control. Fluorescence-activated cell sorting analyses of binding of mAbs 2G12 (Harrison (2008), Supra) Fab, VRC01 (Wyatt and Sodroski, Supra), 2F5, 1281, 98-6D, 126-7D, 167D and 1379 to the envelope trimer expressed on 293T cell surfaces were carried out by incubating these antibodies with transfected cells, followed by detection using a phycoerythrin-conjugated goat anti-human secondary antibody. The histograms (cell counts v. fluorescence intensity) are shown. Significant binding to the 92UG037.8 envelope was only detected for mAbs 2G12 and VRC01. Significant binding was not detected for 2F5 and the cluster II antibodies. The experiments were repeated twice with similar results.

Figure 10A:
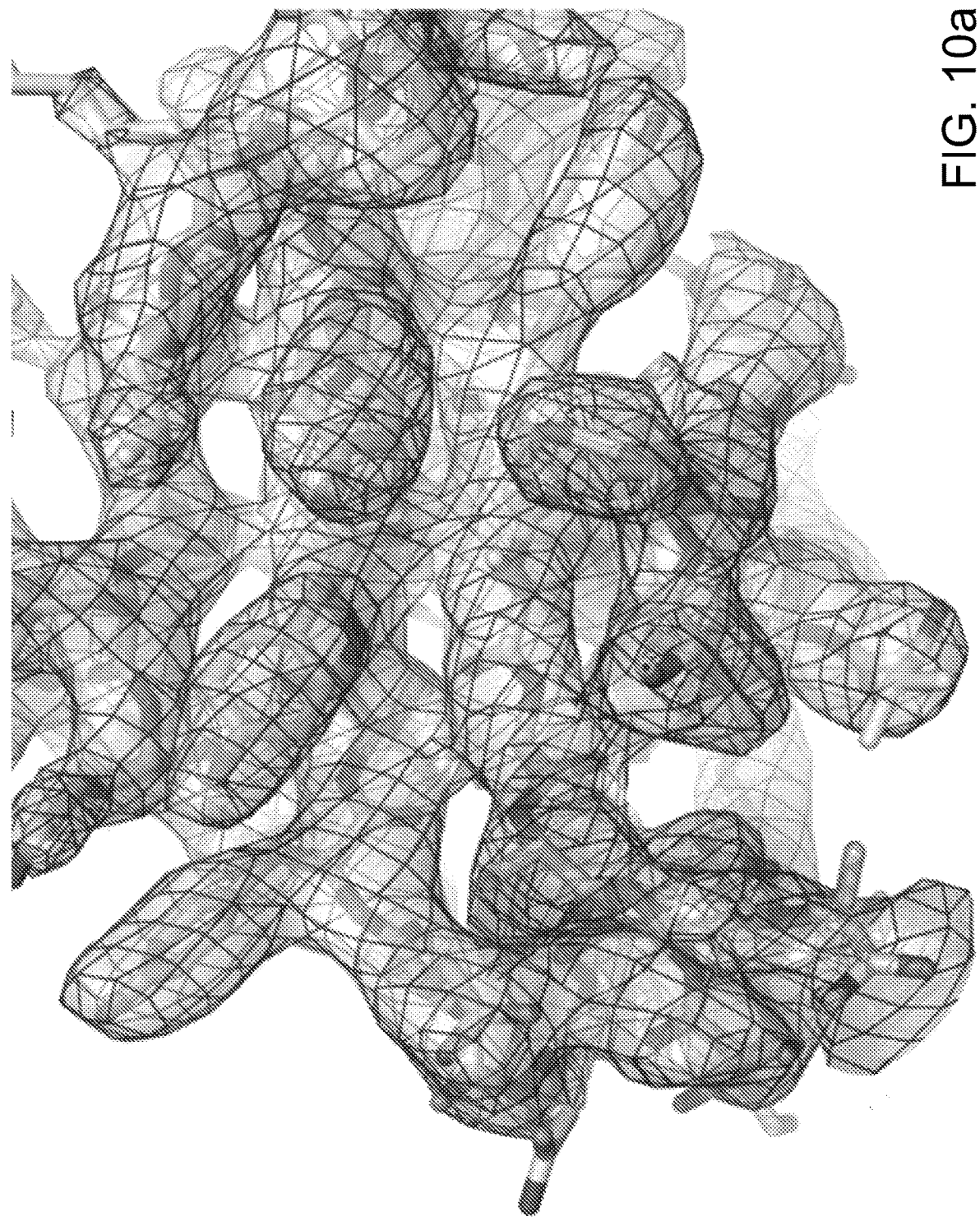
Figure 10B:
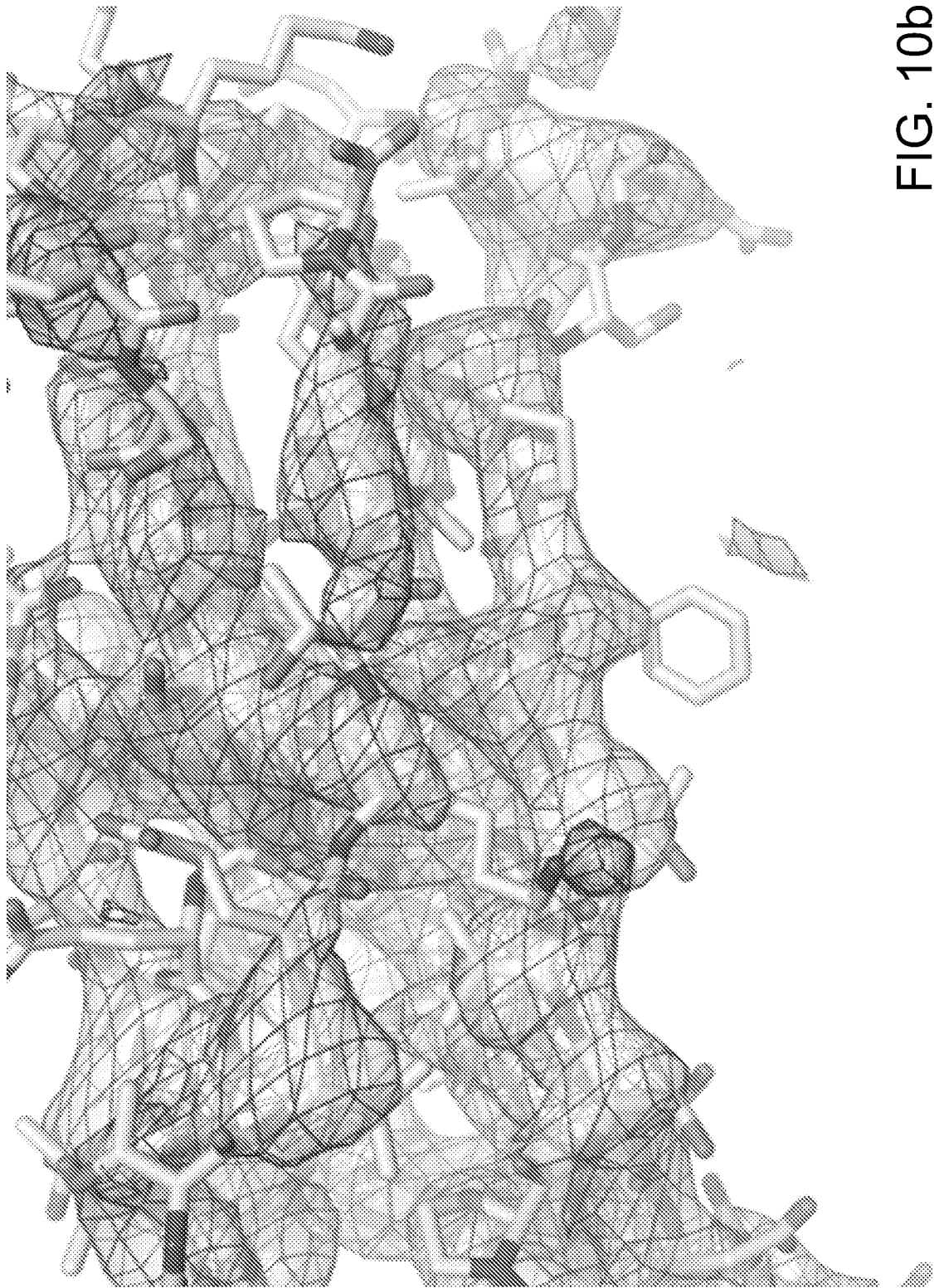
Figure 10C:
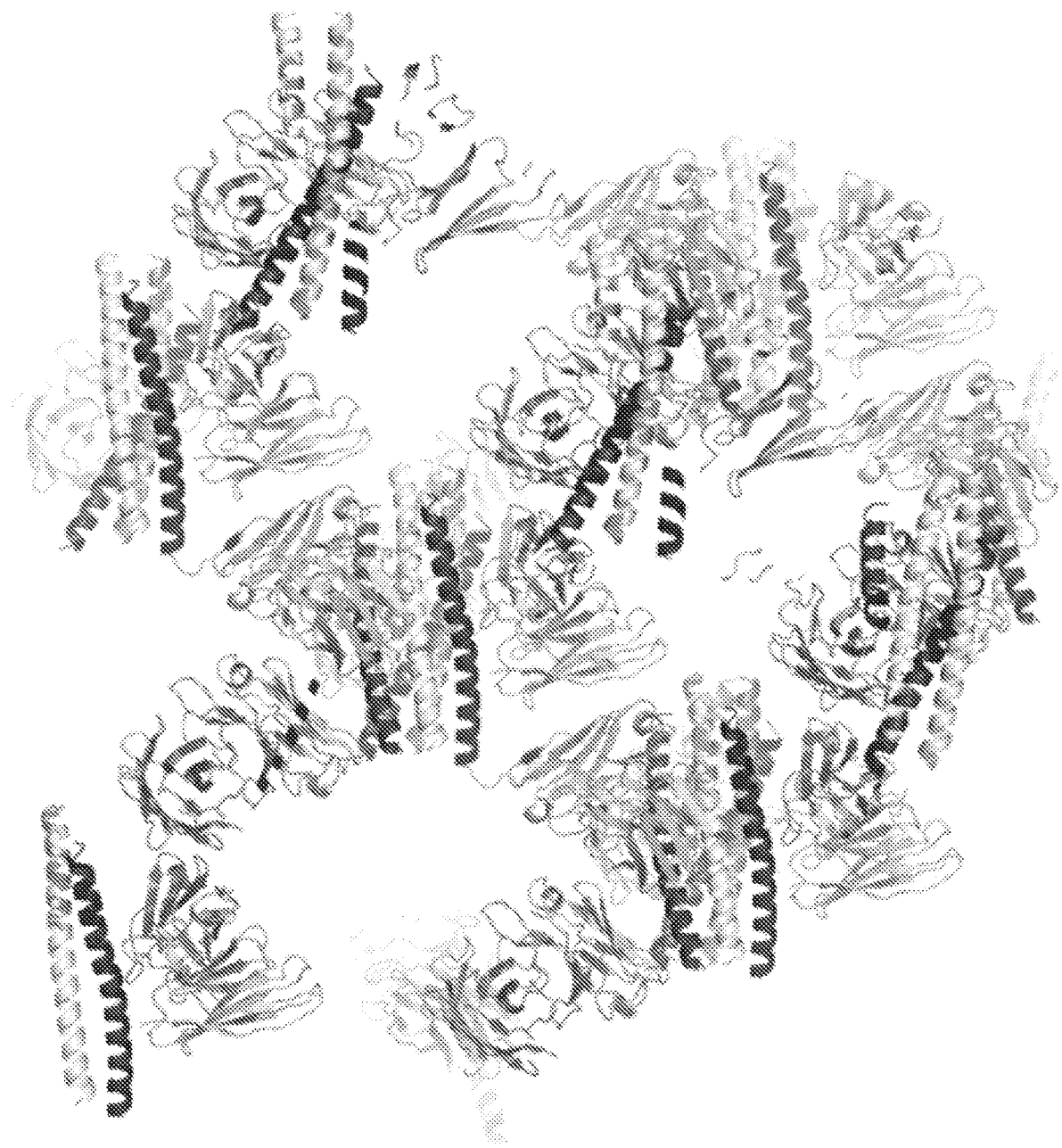

FIGS. 10A-10C schematically depict electron density for the variable and constant domains of 1281 Fab and crystal packing of the gp41-1281 Fab complex. The crystal structure of the complex of the 1281 Fab and gp41-post was solved by molecular replacement and refined to 3.3 Å resolution. Electron density was shown for the variable domain (A) and the constant domain (B) of the 1281 Fab, respectively. Polypeptide chains are shown by stick models and density is in blue. Excellent density was observed for the variable region including the CDR loops. Poor density throughout the constant domain indicated that the entire domain may be in multiple orientations in the crystal lattice. In C, the crystal packing of the complex gp41-1281 Fab is shown. The crystal lattice can form by the variable domain of 1281 Fab and gp41-post in absence of the constant region of the Fab. HR1 of gp41-post is in yellow and HR2 in blue, the variable region of 1281 in green. The empty space is occupied by the constant domain.

DETAILED DESCRIPTION

HIV-1 envelope glycoprotein gp41 undergoes large conformational changes to drive fusion of viral and target cell membranes, thereby exhibiting at least three distinct conformations during the viral entry process. Neutralizing antibodies against gp41 block HIV-1 infection by targeting its membrane proximal external region in a fusion-intermediate state. The present invention is based in part on the discovery that non-neutralizing antibodies, capable of binding with high affinity to an immunodominant segment adjacent to the neutralizing epitopes in the membrane-proximal region, only recognize a gp41 conformation when membrane fusion is complete. These results indicate that the non-neutralizing antibodies are induced in HIV-1 infected subjects by gp41 antigens in a triggered, post-fusion form, and contribute to production of ineffective humoral responses. Based on these results, compositions and methods for gp41-based rational vaccine design are provided.

Embodiments of the present invention are directed to scaffolds for presenting an amino acid sequence or protein, such as heptad repeat regions and/or membrane-proximal external regions, in an immunogenic or antigenic conformation. According to one aspect of the present invention, scaffolds can be altered or designed to maintain the same or a substantially similar amino acid sequence or protein in an immunogenic or antigenic conformation. Different scaffold designs can maintain the same amino acid sequence or protein in an immunogenic or antigenic conformation. In addition, the amino acid sequences or proteins of the present invention can be altered or modified according to methods known in the art to have different sequences yet still be capable of being placed in an immunogenic or antigenic conformation. It is to be understood that the specific amino acid sequences and proteins described herein include sequences and proteins that are substantially similar or homologous thereto or those that can be modified in a manner contemplated by those skilled in the art without departing from the spirit and operation of the invention.

Accordingly, the present invention is directed in part to pre-hairpin intermediate conformations of the envelope protein (e.g., gp41) of a human immunodeficiency virus (e.g., HIV-1) and methods for their use. In certain exemplary embodiments, the compounds and methods described herein are used to inhibit or decrease one or more HIV-mediated activities (e.g., infection, fusion (e.g., target cell entry and/or syncytia formation), viral spread and the like) in a subject, which can, in turn, decrease HIV titer.

As used herein, the terms "inhibiting" or "decreasing" with respect to HIV refer to an inhibition or decrease of an HIV-mediated activity (e.g., infection, fusion (e.g., target cell entry and/or syncytia formation), viral spread and the like) and/or a decrease in viral titer. For example, an HIV-mediated activity may be decreased by 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% (or any ranges therein) or more.

HIV is a member of the genus Lentivirinae, part of the family of Retroviridae. Two species of HIV infect humans: HIV-1 and HIV-2. As used herein, the terms "human immunodeficiency virus" and "HIV" refer, but are not limited to, HIV-1 and HIV-2. In certain exemplary embodiments, the envelope proteins described herein refer to those present on any of the five serogroups of lentiviruses that are recognized: primate (e.g., HIV-1, HIV-2, simian immunodeficiency virus (SIV)); sheep and goat (e.g., visna virus, caprine arthritis encephalitis virus); horse (equine infectious anemia virus); cat (e.g., feline immunodeficiency virus (FIV)); and cattle (e.g., bovine immunodeficiency virus (BIV)) (See International Committee on Taxonomy of Viruses descriptions).

HIV is categorized into multiple clades with a high degree of genetic divergence. As used herein, the term "clade"

refers to related human immunodeficiency viruses classified according to their degree of genetic similarity. There are currently three groups of HIV-1 isolates: M, N, and O. Group M (major strains) consists of at least ten clades, A through J. Group O (outer strains) may consist of a similar number of clades. Group N is a new HIV-1 isolate that has not been categorized in either group M or O. In certain exemplary embodiments, a broadly neutralizing antibody described herein will recognize and raise an immune response against two, three, four, five, six, seven, eight, nine, ten or more clades and/or two or more groups of HIV.

As used herein, the term "envelope glycoprotein" refers, but is not limited to, the glycoprotein that is expressed on the surface of the envelope of HIV virions and the surface of the plasma membrane of HIV infected cells. The env gene encodes gp160, which is proteolytically cleaved into gp120 and gp140. Gp120 binds to the CD4 receptor on a target cell that has such a receptor, such as, e.g., a T-helper cell. Gp41 is non-covalently bound to gp120, and provides the second step by which HIV enters the cell. It is originally buried within the viral envelope, but when gp120 binds to a CD4 receptor, gp120 changes its conformation causing gp41 to become exposed, where it can assist in fusion with the host cell.

In certain exemplary embodiments, a pre-hairpin intermediate conformation of an HIV envelope glycoprotein (e.g., gp41) is provided. As used herein, the term "pre-hairpin intermediate conformation" refers, but is not limited to, the form of an envelope glycoprotein, e.g., of gp41, that is present during the transition from the "pre-fusion" conformation of the envelope glycoprotein, as is found on infectious virions, to the "post-fusion" conformation, the final, stable conformation after viral entry into a target cell is complete. In certain aspects, a pre-hairpin intermediate conformation of an envelope protein includes one or more oligomerization domains, one or more or more heptad repeat 2 (HR2) motifs (e.g., from any HIV-1 isolate), and one or more membrane-proximal external regions (MPER) (e.g., from any HIV-1 isolate). In certain optional aspects, a pre-hairpin intermediate conformation of an envelope protein further includes one or more linker regions. In other optional aspects, a pre-hairpin intermediate conformation of an envelope protein includes one or more C-C loop domains (e.g., from any HIV-1 isolate). In certain aspects, a pre-hairpin intermediate conformation of an envelope protein excludes a heptad repeat 1 (HR1) region. In other aspects, a pre-hairpin intermediate conformation of an envelope protein excludes an HR1 helix. In yet other aspects, a pre-hairpin intermediate conformation of an envelope protein excludes an HR1-HR2 six helix bundle. In certain exemplary embodiments, a pre-hairpin intermediate conformation of an envelope protein includes one or more of the specific constructs described further herein (Infra).

In certain exemplary embodiments, a pre-hairpin intermediate conformation of an envelope protein comprises the entire polypeptide sequence set forth as SEQ ID NO:1. In certain exemplary embodiments, a pre-hairpin intermediate conformation of an envelope protein consists essentially of the entire polypeptide sequence set forth as SEQ ID NO:1. In certain exemplary embodiments, a pre-hairpin intermediate conformation of an envelope protein consists of the entire polypeptide sequence set forth as SEQ ID NO:1. In certain exemplary embodiments, a pre-hairpin intermediate conformation of an envelope protein includes one or more portions of the polypeptide sequence set forth as SEQ ID NO:1 (e.g., truncations, deletions, substitutions, regions from differing HIV-1 isolates and the like). In certain aspects, a pre-hairpin intermediate conformation of an envelope protein has 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% (or any ranges therein) homology to the polypeptide sequence set forth as SEQ ID NO:1. In other aspects, a pre-hairpin intermediate conformation of an envelope protein has 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% (or any ranges therein) homology to the polypeptide sequence of the oligomerization domain set forth in SEQ ID NO:1. In other aspects, a pre-hairpin intermediate conformation of an envelope protein has 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% (or any ranges therein) homology to the polypeptide sequence of the C-C loop set forth in SEQ ID NO:1. In other aspects, a pre-hairpin intermediate conformation of an envelope protein has 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% (or any ranges therein) homology to the polypeptide sequence of HR2 that is set forth in SEQ ID NO: 1. In other aspects, a pre-hairpin intermediate conformation of an envelope protein has 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% (or any ranges therein) homology to the polypeptide sequence to the MPER set forth in SEQ ID NO:1. In other aspects, a pre-hairpin intermediate conformation of an envelope protein has 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% (or any ranges therein) homology to the polypeptide sequence of the foldon tag set forth in SEQ ID NO:1. In other aspects, a pre-hairpin intermediate conformation of an envelope protein has 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% (or any ranges therein) homology to any combination of the polypeptide sequences of the oligomerization domain, the C-C loop, HR2, the MPER and the foldon tag set forth in SEQ ID NO:1.

As used herein, the terms "heptad repeat 1" and "HR1" refer, but are not limited to, a heptad repeat region that is located at the amino terminus of wild-type gp41. As used herein, the terms "heptad repeat 2" and "HR2" refer, but are not limited to, a heptad repeat region that is located at the carboxy terminus of wild-type gp41. A heptad repeat is a motif in which a hydrophobic amino acid is repeated every seven residues; such motifs are designated a through g (Lupas (1996) *Trends Biochem. Sci.* 21:375). Heptad repeats which contain hydrophobic or neutral residues at the a and d positions can form alpha helices and are able to interact with other heptad repeats by forming coiled coils (Chambers et al. (1990) *J. Gen. Virol.* 71:3075; and Lupas, supra). The gp41 HR1 and HR2 sequences are well known in the art and are described in, e.g., Miller et al. (2005) *Proc. Natl. Acad. Sci. USA* 102:14759, incorporated herein by reference in its entirety for all purposes.

As used herein, the terms "membrane-proximal external region" and "MPER" refer, but are not limited to, a highly conserved region of the gp41 ectodomain adjacent to the viral membrane that is well known in the art.

As used herein, the term "C-C loop domain" refers, but is not limited to, an immunodominant loop present in gp41 proteins that has a conserved disulfide bond. The HIV C-C loop domain is well known in the art.

As used herein, the term "oligomerization domain" refers, but is not limited to, a polypeptide sequence that can be used to increase the stability of an oligomeric envelope protein such as, e.g., to increase the stability of an HIV gp41 trimer. Oligomerization domains may increase the stability of dimers, trimers, tetramers, pentamers, hexamers, heptamers, octamers, nonamers, decamers and larger oligomers. In certain aspects, oligomerization domains increase the stability of trimers. Oligomerization domains can be used to increase the stability of homooligomeric polypeptides as well as heterooligomeric polypeptides. Oligomerization domains are well known in the art.

Examples of oligomerization domains (e.g., trimerization domains) include, but are not limited to, the T4-fibritin "foldon" trimer; the coiled-coil trimer derived from GCN4 (Yang et al. (2002) *J. Virol.* 76:4634); human collagen trimerization tag (Fan et al. (2008) *The FASEB Journal* 22:3795); the catalytic subunit of *E. coli* aspartate transcarbamoylase as a trimer tag (Chen et al. (2004) *J. Virol.* 78:4508), AP-1(-like) components (e.g., Jun, Fos), AP-1(-like) (e.g., GCN4), CRE-BP/ATF, CREB (e.g., CREB, ATF-1), C/EBP-like factors, cell-cycle controlling factors (e.g., Myc, Max), and many viral fusion proteins. Oligomerization domains are well known in the art.

As used herein, the term "protein tag" refers, but is not limited to, a polypeptide sequence that can be added to another polypeptide sequence for a variety of purposes. In certain exemplary embodiments, a protein tag may be removed from a larger polypeptide sequence when it is no longer needed. Protein tags include, but are not limited to, affinity tags (e.g., poly-His tags, chitin binding protein (CBP), maltose binding protein (MBP), glutathione-s-transferase (GST) and the like), solubilization tags (e.g., include thioredoxin (TRX), poly(NANP) MBP, GST and the like), chromatography tags (e.g., polyanionic amino acids such as the FLAG epitope), epitope tags (e.g., FLAG-tag, V5-tag, c-myc-tag, HA-tag and the like), fluorescent tags (e.g., green fluorescent protein (GFP), yellow fluorescent protein (YFP), cyan fluorescence protein (CFP) and the like), bioluminescent tags (e.g., luciferase (e.g., bacterial, firefly, click beetle, sea pansy (Renilla) and the like), luciferin, aequorin and the like), enzyme modification tags (e.g., biotin ligase and the like) and the like. Protein tags are well known in the art and their reagents are often commercially available.

In certain exemplary embodiments, a pre-hairpin intermediate conformation of an envelope glycoprotein described herein can be administered to a subject in whom it is desirable to promote an immune response. In other exemplary embodiments, a nucleic acid sequence encoding one or more pre-hairpin intermediate conformations of an envelope protein described herein can be administered to a subject in whom it is desirable to promote an immune response.

Accordingly, one or more pre-hairpin intermediate conformations of envelope glycoprotein(s) can be used as immunogens to produce anti-pre-hairpin intermediate conformation antibodies in a subject, to inhibit or prevent infection by HIV and/or to inhibit or prevent the spread of HIV in an infected individual. One or more pre-hairpin intermediate conformations of an envelope glycoprotein described herein can be used as an immunogen to generate antibodies that bind wild-type envelope glycoprotein (i.e., gp41 and/or gp160) using standard techniques for polyclonal and monoclonal antibody preparation.

In certain exemplary embodiments, a pre-hairpin intermediate conformation of an envelope glycoprotein is capable of eliciting a broadly neutralizing antibody response in a subject. As used herein, the term "broadly neutralizing antibody response" is well known in the art and refers to the ability of one or more antibodies to react with an infectious agent to destroy or greatly reduce the virulence of the infectious agent. The presence of such a response has the potential to prevent the establishment of infection and/or to significantly reduce the number of cells that become infected with HIV, potentially delaying viral spread and allowing for a better control of viral replication in the infected subject. A broadly neutralizing antibody against HIV will typically bind a variety of different clades, groups or mutants of HIV.

In certain exemplary embodiments, a pre-hairpin intermediate conformation of an envelope glycoprotein substantially fails to elicit production of weak and/or non-neutralizing antibodies when present in a subject. As used herein, the terms "weak antibody" and "non-neutralizing antibody" refer to an antibody that fails to react with an infectious agent in a manner such that the infectious agent is destroyed or its virulence is reduced. In certain aspects, a weak antibody or a non-neutralizing antibody reduces the virulence of an infectious agent (e.g., HIV-1) by 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1% or less (or any ranges therein). In certain aspects, a weak antibody or a non-neutralizing antibody kills less than 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1% or fewer (or any ranges therein) of infectious agents (e.g., virions) and/or infected cells present in a subject.

As used herein, the term "substantially fails to elicit production of weak and/or non-neutralizing antibodies" mean that, of a population of antibodies elicited in an individual or host in response to contact with a pre-hairpin intermediate conformation of an envelope glycoprotein, 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1% or fewer (or any ranges therein) of the population of antibodies is weak and/or non-neutralizing against an infectious agent, e.g., HIV-1. Stated differently, 51%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more (or any ranges therein) of the population of antibodies is neutralizing against an infectious agent, e.g., HIV-1, when a pre-hairpin intermediate conformation of an envelope glycoprotein substantially fails to elicit production of weak and/or non-neutralizing antibodies.

Weak and/or non-neutralizing antibodies, for example, include antibodies that bind to the post-fusion conformation of gp41. In certain aspects, weak and/or non-neutralizing antibodies include cluster II antibodies. As used herein, the term "cluster II antibody" refers to an antibody that is produced against an antigenic region between amino acids 644 and 663 of HIV-1 gp41 and/or an antibody that binds to the HR1 helix portion of an HR1-HR2 helical bundle (i.e., the post-fusion conformation) of HIV-1 gp41. Cluster II antibodies include, but are not limited to the following monoclonal antibodies (mAbs): 98-6, 126-6, 167-D, 1281 and 1379. Cluster II antibodies are described in detail in Xu et al. (1991) *J. Virol.* 65:4832, incorporated herein by reference in its entirety for all purposes.

As used herein, the term "immune response" is intended to include, but is not limited to, T and/or B cell responses, that is, cellular and/or humoral immune responses. The immune response of a subject can be determined by, for example, assaying antibody production, immune cell proliferation, the release of cytokines, the expression of cell surface markers, cytotoxicity, and the like. As used herein, the term "immune cell" is intended to include, but is not limited to, cells that are of hematopoietic origin and play a role in an immune response Immune cells include, but are not limited to, lymphocytes, such as B cells and T cells; natural killer cells; myeloid cells, such as monocytes, macrophages, eosinophils, mast cells, basophils, and granulocytes.

A pre-hairpin intermediate conformation of an envelope glycoprotein typically is used to prepare antibodies by immunizing a suitable subject, (e.g., human rabbit, goat, mouse or other mammal) with the immunogen. An appropriate immunogenic preparation can contain, for example, a recombinantly expressed pre-hairpin intermediate conformation of an envelope glycoprotein or a chemically synthesized pre-hairpin intermediate conformation of an envelope glycoprotein. The preparation can further include an adjuvant, such as Freund's complete or incomplete adjuvant, or similar immunostimulatory agent. Immunization of a suitable subject with an immunogenic pre-hairpin intermediate conformation of an envelope glycoprotein preparation induces a polyclonal anti-envelope (e.g., anti-gp41 and/or anti-gp160) antibody response, e.g., an anti-HIV antibody response.

Accordingly, in certain exemplary embodiments, anti-pre-hairpin intermediate conformation of gp41 antibodies are provided. The term "antibody" as used herein refers to immunoglobulin molecules and immunologically active portions of immunoglobulin molecules, i.e., molecules that contain an antigen binding site which specifically binds (immunoreacts with) an antigen, such as the envelope glycoprotein (e.g., gp41 and/or gp160). Examples of immunologically active portions of immunoglobulin molecules include F(ab) and F(ab')2 fragments which can be generated by treating the antibody with an enzyme such as pepsin. The invention provides polyclonal and monoclonal antibodies that bind the envelope glycoprotein (e.g., gp41 and/or gp160). The term "monoclonal antibody" or "monoclonal antibody composition," as used herein, refers to a population of antibody molecules that contain only one species of an antigen binding site capable of immunoreacting with a particular epitope of the envelope glycoprotein (e.g., gp41 and/or gp160). A monoclonal antibody composition thus typically displays a single binding affinity for a particular the envelope glycoprotein (e.g., gp41 and/or gp160) with which it immunoreacts.

Polyclonal anti-envelope glycoprotein (e.g., gp41 and/or gp160) antibodies can be prepared as described above by immunizing a suitable subject with a pre-hairpin intermediate conformation of an envelope glycoprotein immunogen as described herein. In certain aspects, a pre-hairpin intermediate conformation of an envelope glycoprotein immunogen is present in a single (e.g., antigenic) conformation, e.g., substantially all of the glycoprotein immunogens have an HR2 positioned in pre-hairpin intermediate conformation and/or lack an HR1-HR2 six helix bundle.

The anti-pre-hairpin intermediate conformation of an envelope glycoprotein antibody titer in the immunized subject can be monitored over time by standard techniques, such as with an enzyme linked immunosorbent assay (ELISA) using immobilized gp41. If desired, the antibody molecules directed against gp41 can be isolated from the mammal (e.g., from the blood) and further purified by well known techniques, such as protein A chromatography to obtain the IgG fraction. At an appropriate time after immunization, e.g., when the anti-gp41 antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the human B cell hybridoma technique (Kozbor et al. (1983) *Immunol. Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.* 54:387-402; Gefter et al. (1977) *Somatic Cell Genet.* 3:231-36). Briefly, an immortal cell line (typically a myeloma) is fused to lymphocytes (typically splenocytes) from a mammal immunized with a pre-hairpin intermediate conformation of an envelope glycoprotein immunogen as described above, and the culture supernatants of the resulting hybridoma cells are screened to identify a hybridoma producing a monoclonal antibody that binds gp41.

Any of the many well known protocols used for fusing lymphocytes and immortalized cell lines can be applied for the purpose of generating an anti-pre-hairpin intermediate conformation of an envelope glycoprotein monoclonal antibody (see, e.g., G. Galfre et al. (1977) *Nature* 266:55052; Gefter et al. *Somatic Cell Genet.*, cited supra; Lerner, *Yale J. Biol. Med.* (supra); Kenneth, *Monoclonal Antibodies*, (supra)). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Particularly suitable immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of a pre-hairpin intermediate conformation of an envelope glycoprotein are detected by screening the hybridoma culture supernatants for antibodies that bind gp41, e.g., using a standard ELISA assay.

Alternative to preparing monoclonal antibody-secreting hybridomas, a monoclonal anti-pre-hairpin intermediate conformation of an envelope glycoprotein antibody can be identified and isolated by screening a recombinant combinatorial immunoglobulin library (e.g., an antibody phage display library) with a gp41 protein to thereby isolate immunoglobulin library members that bind gp41. Kits for generating and screening phage display libraries are commercially available (e.g., Recombinant Phage Antibody System, Pfizer, New York, N.Y.; and the SURFZAP™ Phage Display Kit, Stratagene, La Jolla, Calif.). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrad et al. (1991) *Bio/Technology* 9:1373-1377; Hoogenboom et al. (1991) *Nucl. Acid Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-pre-hairpin intermediate conformations of envelope glycoprotein antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In certain exemplary embodiments, antibodies, fusion inhibiting agents (e.g., small molecules, peptides and the like) and the like that are capable of interacting with a pre-hairpin intermediate conformation of an HIV envelope glycoprotein are provided. As used herein, the terms "bind," "binding," "interact," "interacting," "occupy" and "occupying" refer to covalent interactions, noncovalent interactions and steric interactions. A covalent interaction is a chemical linkage between two atoms or radicals formed by the sharing of a pair of electrons (a single bond), two pairs of electrons (a double bond) or three pairs of electrons (a triple bond). Covalent interactions are also known in the art as electron pair interactions or electron pair bonds. Noncovalent interactions include, but are not limited to, van der Waals interactions, hydrogen bonds, weak chemical bonds (via short-range noncovalent forces), hydrophobic interactions, ionic bonds and the like. A review of noncovalent interactions can be found in Alberts et al., in *Molecular Biology of the Cell*, 3d edition, Garland Publishing, 1994. Steric interactions are generally understood to include those where the structure of the compound is such that it is capable of occupying a site by virtue of its three dimensional structure, as opposed to any attractive forces between the compound and the site.

In certain exemplary embodiments, compositions and methods for enhancing the immune response of a subject to a human immunodeficiency virus are provided. As used herein, the terms "subject" and "host" are intended to include living organisms such as mammals. Examples of subjects and hosts include, but are not limited to, horses, cows, sheep, pigs, goats, dogs, cats, rabbits, guinea pigs, rats, mice, gerbils, non-human primates (e.g., macaques), humans and the like, non-mammals, including, e.g., non-mammalian vertebrates, such as birds (e.g., chickens or ducks) fish or frogs (e.g., *Xenopus*), and non-mammalian invertebrates, as well as transgenic species thereof.

In certain exemplary embodiments, vectors such as, for example, expression vectors, containing a nucleic acid encoding one or more pre-hairpin intermediate conformations of an envelope protein described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably. However, the invention is intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more pre-hairpin intermediate conformations of an envelope protein described herein) in a form suitable for expression of the nucleic acid sequence in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence encoding one or more pre-hairpin intermediate conformations of an envelope protein is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors described herein can be introduced into host cells to thereby produce proteins or portions thereof, including fusion proteins or portions thereof, encoded by nucleic acids as described herein (e.g., one or more pre-hairpin intermediate conformations of an envelope protein).

In certain exemplary embodiments, nucleic acid molecules described herein can be inserted into vectors and used as gene therapy vectors. Gene therapy vectors can be delivered to a subject by, for example, intravenous injection, local administration (see, e.g., U.S. Pat. No. 5,328,470), or by stereotactic injection (see, e.g., Chen et al. (1994) *Proc. Natl. Acad. Sci. U.S.A.* 91:3054). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, adeno-associated virus vectors, and the like, the pharmaceutical preparation can include one or more cells which produce the gene delivery system (See Gardlik et al. (2005) *Med. Sci. Mon.* 11:110; Salmons and Gunsberg (1993) *Hu. Gene Ther.* 4:129; and Wang et al. (2005) *J. Virol.* 79:10999 for reviews of gene therapy vectors).

Recombinant expression vectors of the invention can be designed for expression of one or more encoding one or more pre-hairpin intermediate conformations of an envelope protein in prokaryotic or eukaryotic cells. For example, one or more vectors encoding one or more pre-hairpin intermediate conformations of an envelope protein can be expressed in bacterial cells such as *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40); pMAL (New England Biolabs, Beverly, Mass.); and pRIT5 (Pharmacia, Piscataway, N.J.) which fuse glutathione S-transferase (GST), maltose E binding protein, or protein A, respectively, to the target recombinant protein.

In another embodiment, the expression vector encoding one or more pre-hairpin intermediate conformations of an envelope protein is a yeast expression vector. Examples of vectors for expression in yeast *S. cerevisiae* include pYepSec1 (Baldari, et. al., (1987) *EMBO J.* 6:229-234); pMFa (Kurjan and Herskowitz, (1982) *Cell* 30:933-943); pJRY88 (Schultz et al., (1987) *Gene* 54:113-123); pYES2 (Invitrogen Corporation, San Diego, Calif.); and picZ (Invitrogen Corporation).

Alternatively, one or more pre-hairpin intermediate conformations of an envelope protein can be expressed in insect cells using baculovirus expression vectors. Baculovirus vectors available for expression of proteins in cultured insect cells (e.g., Sf9 cells) include the pAc series (Smith et al. (1983) *Mol. Cell Biol.* 3:2156-2165) and the pVL series (Lucklow and Summers (1989) *Virology* 170:31-39).

In certain exemplary embodiments, a nucleic acid described herein is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, adenovirus 2, cytomegalovirus and simian virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

In certain exemplary embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include lymphoid-specific promoters (Calame and Eaton (1988) *Adv. Immunol.* 43:235), in particular promoters of T cell receptors (Winoto and Baltimore (1989) *EMBO J.* 8:729) and immunoglobulins (Banerji et al. (1983) *Cell* 33:729; Queen and Baltimore (1983) *Cell* 33:741), neuron-specific promoters (e.g., the neurofilament promoter; Byrne and Ruddle (1989) *Proc. Natl. Acad. Sci. U.S.A.* 86:5473), pancreas-specific promoters (Edlund et al. (1985) *Science* 230:912), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374) and the α-fetoprotein promoter (Campes and Tilghman (1989) *Genes Dev.* 3:537).

In certain exemplary embodiments, host cells into which a recombinant expression vector of the invention has been introduced are provided. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, one or more pre-hairpin intermediate conformations of an envelope protein can be expressed in bacterial cells such as E. coli, viral cells such as retroviral cells, insect cells, yeast or mammalian cells (such as Chinese hamster ovary cells (CHO) or COS cells). Other suitable host cells are known to those skilled in the art.

Delivery of nucleic acids described herein (e.g., vector DNA) can be by any suitable method in the art. For example, delivery may be by injection, gene gun, by application of the nucleic acid in a gel, oil, or cream, by electroporation, using lipid-based transfection reagents, or by any other suitable transfection method.

As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENE® (Roche Applied Science, Basel, Switzerland), JETPEI™ (Polyplus-transfection Inc., New York, N.Y.), EFFECTENE® (Qiagen, Valencia, Calif.), DREAM-FECT™ (OZ Biosciences, France) and the like), or electroporation (e.g., in vivo electroporation). Suitable methods for transforming or transfecting host cells can be found in Sambrook, et al. (*Molecular Cloning: A Laboratory Manual.* 2nd, ed., Cold Spring harbor Laboratory, Cold Spring Harbor Laboratory Press, Cold Spring Harbor, N.Y., 1989), and other laboratory manuals.

Embodiments of the invention are directed to a first nucleic acid (e.g., a nucleic acid sequence encoding one or more gp41 domains or motifs such as, for example, HR1 from a wild type gp41 strain, HR2 from a wild type gp41 strain, MPER from a wild type gp41 strain and the like) or polypeptide sequence (e.g., one or more gp41 domains or motifs such as, for example, HR1 from a wild type gp41 strain, HR2 from a wild type gp41 strain, MPER from a wild type gp41 strain and the like) having a certain sequence identity or percent homology to a second nucleic acid or polypeptide sequence, respectively.

Techniques for determining nucleic acid and amino acid "sequence identity" are known in the art. Typically, such techniques include determining the nucleotide sequence of genomic DNA, mRNA or cDNA made from an mRNA for a gene and/or determining the amino acid sequence that it encodes, and comparing one or both of these sequences to a second nucleotide or amino acid sequence, as appropriate. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100.

An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure,* M. O. Dayhoff ed., 5 suppl. 3:353-358, National Biomedical Research Foundation, Washington, D.C., USA, and normalized by Gribskov (1986) *Nucl. Acids Res.* 14:6745. An exemplary implementation of this algorithm to determine percent identity of a sequence is provided by the Genetics Computer Group (Madison, Wis.) in the "BestFit" utility application. The default parameters for this method are described in the *Wisconsin Sequence Analysis Package Program Manual,* Version 8 (1995) (available from Genetics Computer Group, Madison, Wis.).

One method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated the "match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cut-off=60; expect=10; Matrix=BLOSUM62; Descriptions=50 sequences; sort by =HIGH SCORE; Databases=non-redundant, GenBank+EMBL+DDBJ+PDB+GenBank CDS translations+Swiss protein+Spupdate+PIR. Details of these programs can be found at the NCBI/NLM web site.

Alternatively, homology can be determined by hybridization of polynucleotides under conditions that form stable duplexes between homologous regions, followed by digestion with single-stranded-specific nuclease(s), and size determination of the digested fragments. Two DNA sequences, or two polypeptide sequences are "substantially homologous" to each other when the sequences exhibit at least about 80%-85%, at least about 85%-90%, at least about 90%-95%, or at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., *Molecular Cloning: A Laboratory Manual,* Second Edition, (1989) Cold Spring Harbor, N.Y.; *Nucleic Acid Hybridization: A Practical Approach,* editors B. D. Hames and S. J. Higgins, (1985) Oxford; Washington, D.C.; IRL Press.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule Inhibition of hybridization of the completely identical sequence can be assessed using hybridization assays that are well known in the art (e.g., Southern blot, Northern blot, solution hybridization, or the like, see Sambrook, et al., supra). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, Nucleic Acid Hybridization, Supra).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as varying wash conditions. The selection of a particular set of hybridization conditions is selected following standard methods in the art (see, for example, Sambrook et al., Supra).

As used herein, the term "hybridizes under stringent conditions" is intended to describe conditions for hybridization and washing under which nucleotide sequences at least 60% identical to each other typically remain hybridized to each other. In one aspect, the conditions are such that sequences at least about 70%, at least about 80%, at least about 85% or 90% or more identical to each other typically remain hybridized to each other. Such stringent conditions are known to those skilled in the art and can be found in *Current Protocols in Molecular Biology*, John Wiley & Sons, NY (1989), 6.3.1-6.3.6. A non-limiting example of stringent hybridization conditions are hybridization in 6× sodium chloride/sodium citrate (SSC) at about 45° C., followed by one or more washes in 0.2×SSC, 0.1% SDS at 50° C., at 55° C., or at 60° C. or 65° C.

A first polynucleotide is "derived from" a second polynucleotide if it has the same or substantially the same base-pair sequence as a region of the second polynucleotide, its cDNA, complements thereof, or if it displays sequence identity as described above. A first polypeptide is derived from a second polypeptide if it is encoded by a first polynucleotide derived from a second polynucleotide, or displays sequence identity to the second polypeptides as described above. In the present invention, when a gp41 protein is "derived from HIV" the gp41 protein need not be explicitly produced by the virus itself, the virus is simply considered to be the original source of the gp41 protein and/or nucleic acid sequences that encode it. Gp41 proteins can, for example, be produced recombinantly or synthetically, by methods known in the art, or alternatively, gp41 proteins may be purified from HIV-infected cell cultures.

In certain exemplary embodiments screening assays for identifying modulators, i.e., candidate or test compounds or agents (e.g., antibodies, peptides, cyclic peptides, peptidomimetics, small molecules, small organic molecules, or other drugs) which have an inhibitory effect on gp41 and/or one or more HIV-mediated activities described herein (e.g., one or more pre-hairpin intermediate conformations of an envelope protein) are provided.

As used herein, the term "small molecule" refers to a molecule, either naturally occurring or synthetic, that has a molecular weight of more than about 25 daltons and less than about 3000 daltons, usually less than about 2500 daltons, more usually less than about 2000 daltons, usually between about 100 to about 1000 daltons, more usually between about 200 to about 500 daltons.

In certain exemplary embodiments, assays for screening candidate or test compounds which bind to or modulate (e.g., inhibit) one or more pre-hairpin intermediate conformations of an envelope protein are provided. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

The test compound(s), antibodies, one or more pre-hairpin intermediate conformations of an envelope protein and/or nucleic acid sequences encoding one or more pre-hairpin intermediate conformations of an envelope protein described herein can be incorporated into pharmaceutical compositions suitable for administration. Such compositions typically comprise the nucleic acid molecule or protein and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In certain exemplary embodiments, a pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the test compound(s), one or more antibodies, one or more pre-hairpin intermediate conformations of an envelope protein and/or nucleic acid sequences encoding one or more pre-hairpin intermediate conformations of an envelope protein described herein in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: A binder such as microcrystalline cellulose, gum tragacanth or gelatin; an excipient such as starch or lactose, a disintegrating agent such as alginic, acid, Primogel, or corn starch; a lubricant such as magnesium stearate or Sterotes; a glidant: such as colloidal silicon dioxide; a sweetening agent such as sucrose or saccharin; or a flavoring agent such as peppermint, methyl salicylate, or orange flavoring.

In one embodiment, the test compound(s), one or more antibodies, one or more pre-hairpin intermediate conformations of an envelope protein and/or nucleic acid sequences encoding one or more pre-hairpin intermediate conformations of an envelope protein described herein are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

Nasal compositions generally include nasal sprays and inhalants. Nasal sprays and inhalants can contain one or more active components and excipients such as preservatives, viscosity modifiers, emulsifiers, buffering agents and the like. Nasal sprays may be applied to the nasal cavity for local and/or systemic use. Nasal sprays may be dispensed by a non-pressurized dispenser suitable for delivery of a metered dose of the active component. Nasal inhalants are intended for delivery to the lungs by oral inhalation for local and/or systemic use. Nasal inhalants may be dispensed by a closed container system for delivery of a metered dose of one or more active components.

In one embodiment, nasal inhalants are used with an aerosol. This is accomplished by preparing an aqueous aerosol, liposomal preparation or solid particles containing the compound. A non-aqueous (e.g., fluorocarbon propellant) suspension could be used. Sonic nebulizers may be used to minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The test compound(s), one or more antibodies, one or more pre-hairpin intermediate conformations of an envelope protein and/or nucleic acid sequences encoding one or more pre-hairpin intermediate conformations of an envelope protein described herein can also be prepared in the form of suppositories (e.g., with conventional suppository bases such as cocoa butter and other glycerides) or retention enemas for rectal delivery.

In one embodiment, the test compound(s), one or more antibodies, one or more pre-hairpin intermediate conformations of an envelope protein and/or nucleic acid sequences encoding one or more one or more pre-hairpin intermediate conformations of an envelope protein described herein are prepared with carriers that will protect them against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of the test compound(s), one or more antibodies, one or more pre-hairpin intermediate conformations of an envelope protein and/or nucleic acid sequences encoding one or more one or more pre-hairpin intermediate conformations of an envelope protein described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from cell culture assays and/or animal studies can be used in formulating a range of dosage for use in humans. The dosage typically will lie within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In certain exemplary embodiments, a method for treatment of a viral infection, e.g., HIV infection, includes the step of administering a therapeutically effective amount of an agent (e.g., one or more test compounds, one or more antibodies, one or more pre-hairpin intermediate conformations of an envelope protein, a nucleic acid sequence that encodes one or more pre-hairpin intermediate conformations of an envelope protein and the like) which modulates (e.g., inhibits), one or more envelope protein (e.g., gp41) activities (e.g., mediating viral fusion (e.g., viral entry and/or syncytia formation)) to a subject. As defined herein, a therapeutically effective amount of agent (i.e., an effective dosage) ranges from about 0.001 to 30 mg/kg body weight, from about 0.01 to 25 mg/kg body weight, from about 0.1 to 20 mg/kg body weight, or from about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an inhibitor can include a single treatment or, in certain exemplary embodiments, can include a series of treatments. It will also be appreciated that the effective dosage of inhibitor used for treatment may increase or decrease over the course of a particular treatment. Changes in dosage may result from the results of diagnostic assays as described herein. The pharmaceutical compositions can be included in a container, pack, or dispenser together with instructions for administration.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures, tables, and accompanying claims.

Example I

Production of GCN4-gp41-Inter

Figure 1:
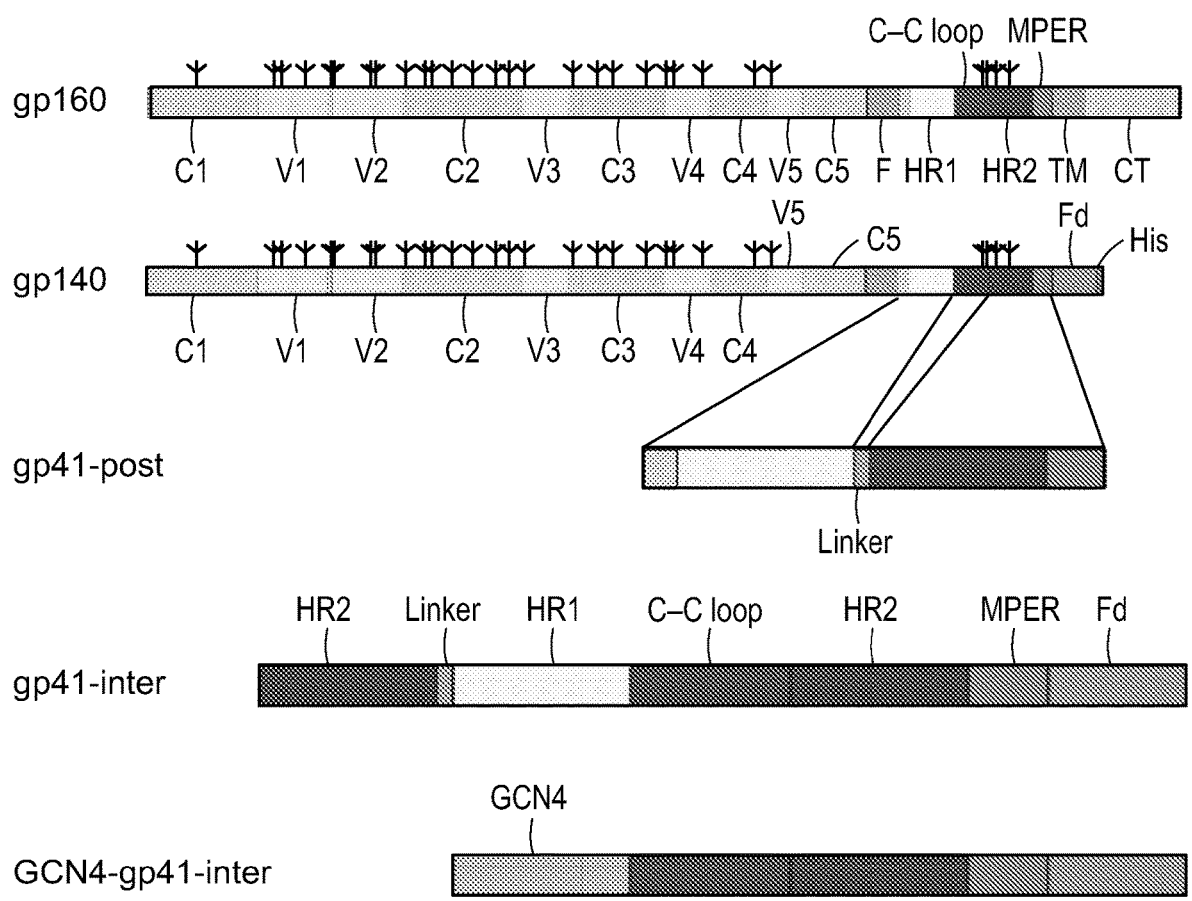
FIG. 1 schematically depicts HIV-1 envelope constructs and GCN4-gp41-inter. Top, schematic representation of HIV-1 envelope glycoprotein gp160, the full-length precursor. Segments of gp120 and gp41 are designated as follows: C1-C5, conserved regions 1-5; V1-V5, variable regions 1-5; F, fusion peptide; HR1, heptad repeat 1; C-C loop, the immunodominant loop with a conserved disulfide bond; HR2, heptad repeat 2; MPER, membrane proximal external region; TM, transmembrane anchor; CT, cytoplasmic tail. Glycans are represented by tree-like symbols. HIV-1 envelope constructs used include gp140, the uncleaved ectodomain of gp160 with a trimerization foldon (Fd) tag and a His-tag at its C-terminus; gp41-post, gp41 in the six helix conformation with partial MPER; gp41-inter, HR2 peptide- and foldon tag-trapped gp41 in the pre-hairpin intermediate conformation; GCN4-gp41-inter, gp41-inter with the six helix bundle portion replaced with a trimeric GCN4 coiled-coil (Harbury et al., Infra) (in light blue). Bottom, diagrams representing 3-D organization of gp41-inter and GCN4-gp41-inter. The trimeric GCN4 with its heptad repeat in the same register as HR1 replaces the HR2-linker-HR1 of gp41-inter. The coordinates of HR1 (Weissenhom et al., Infra) and GCN4 (Harbury et al., Infra) coiled-coils are shown in yellow and light blue, respectively.
Figure 1:
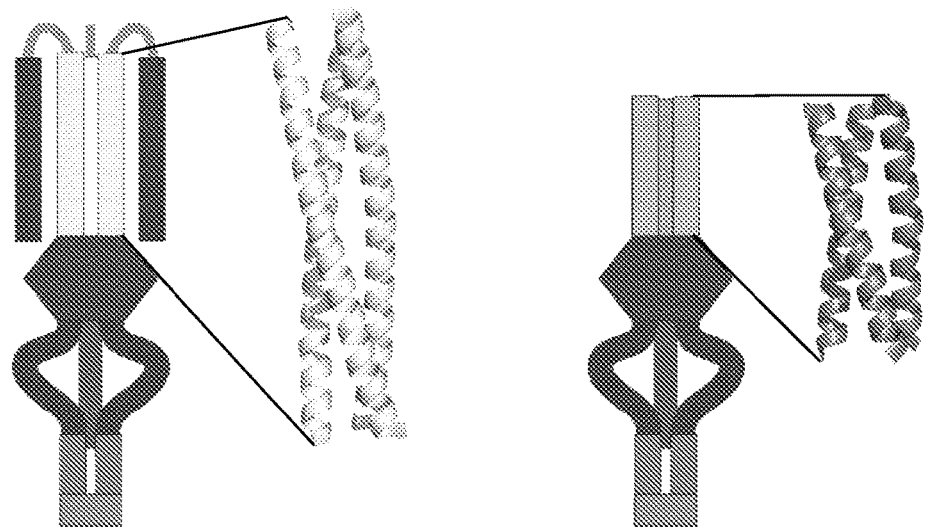
Figure 6:
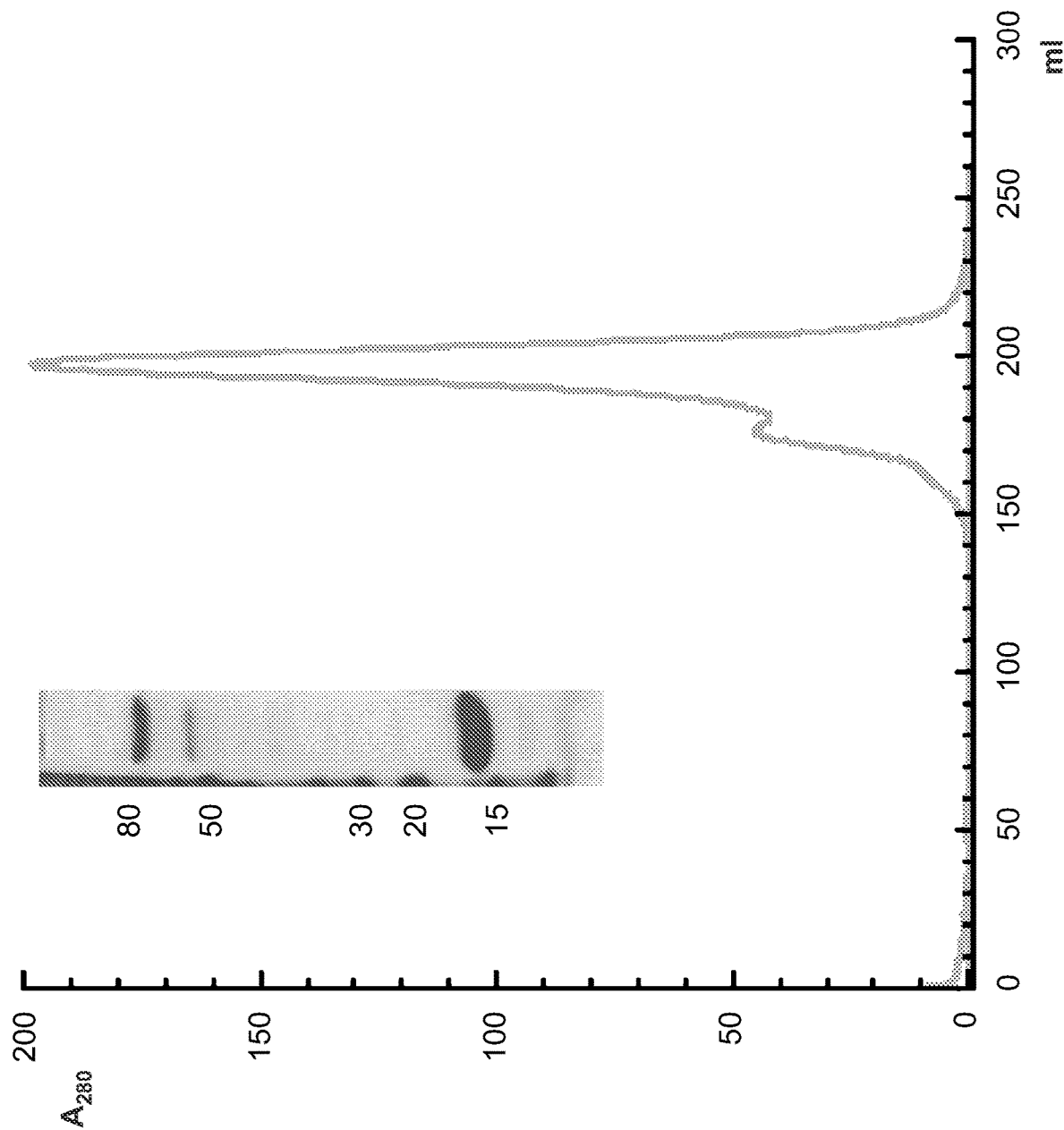
FIG. 6 depicts production of GCN4-41-inter. GCN4-gp41-inter was expressed in *E. coli* and purified by Q-Sepharose under denaturing conditions. The protein was refolded by a rapid-dilution protocol, concentrated and then resolved by gel-filtration chromatography using a prep-grade Superdex 200 column. Peak fractions were pooled and analyzed by Coomassie stained SDS-PAGE (inset). The expected molecular weight for a monomer is 18.7 kDa. Without intending to be bound by scientific theory, the high molecular weight bands are likely the aggregated species in the presence of SDS.
Figure 7A:
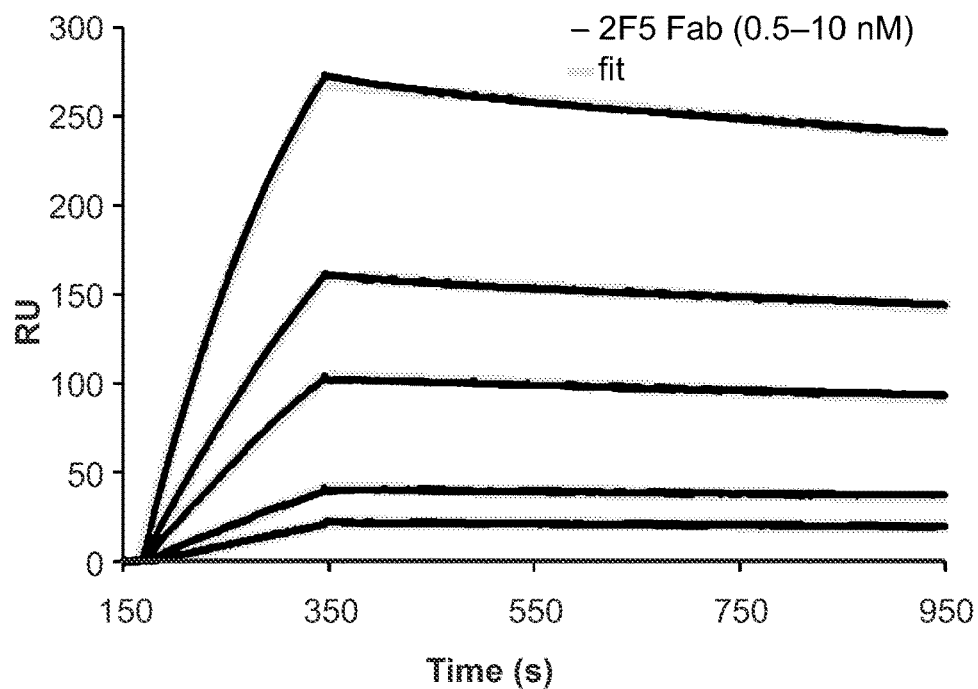
FIGS. 7A-7F graphically compare the MPER conformation in gp41-inter and GCN4-gp41-inter. Conformation of the MPER in gp41-inter and GCN4-gp41-inter was assessed by three MPER-directed, broadly neutralizing monoclonal antibodies, 2F5, 4E10 and Z13e1. Gp41-inter (in A, C and E) or GCN4-gp41-inter (in B, D and F) was immobilized on a CM5 chip surface and Fab fragment derived from each of the three antibodies were passed over each gp41 surface individually. Binding kinetics were analyzed by BiaEvaluation software (Biacore) using 1:1 Langmuir binding model.
Figure 7B:
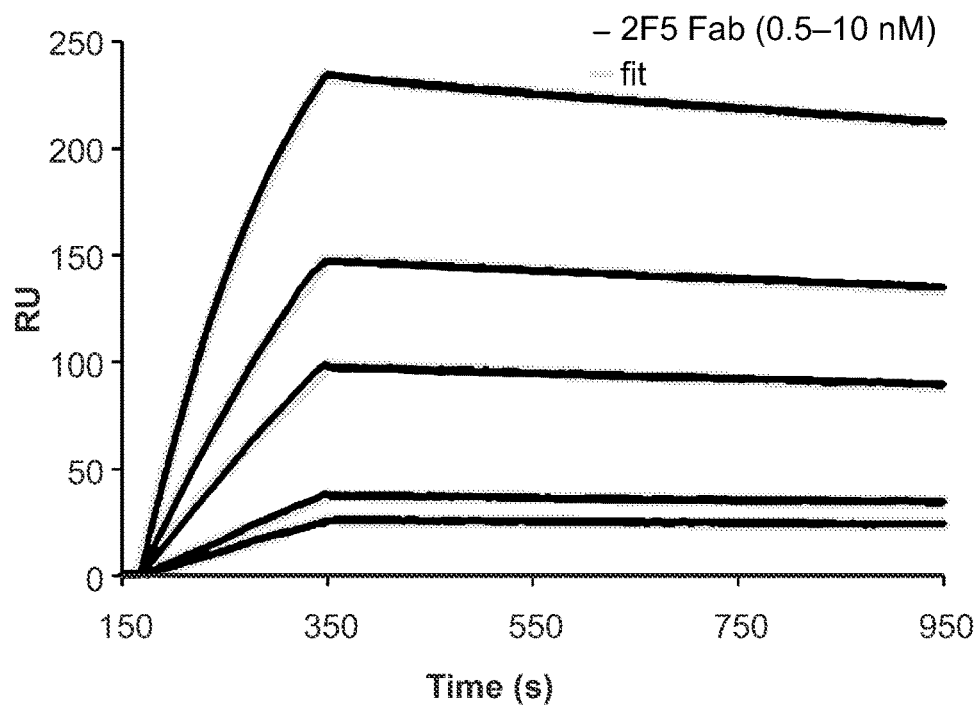
Figure 7C:
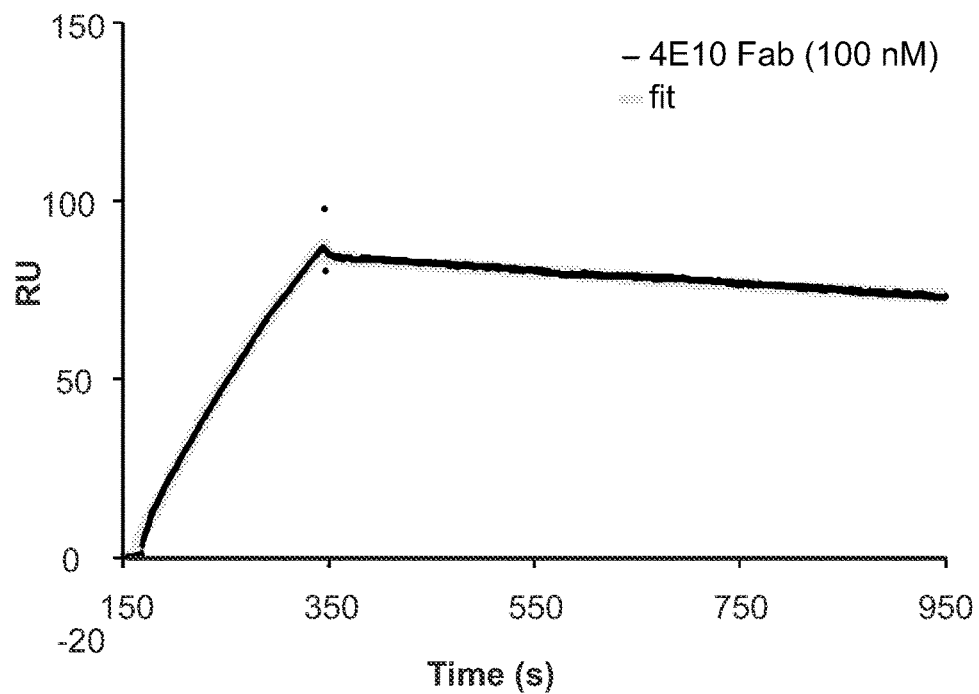
Figure 7D:
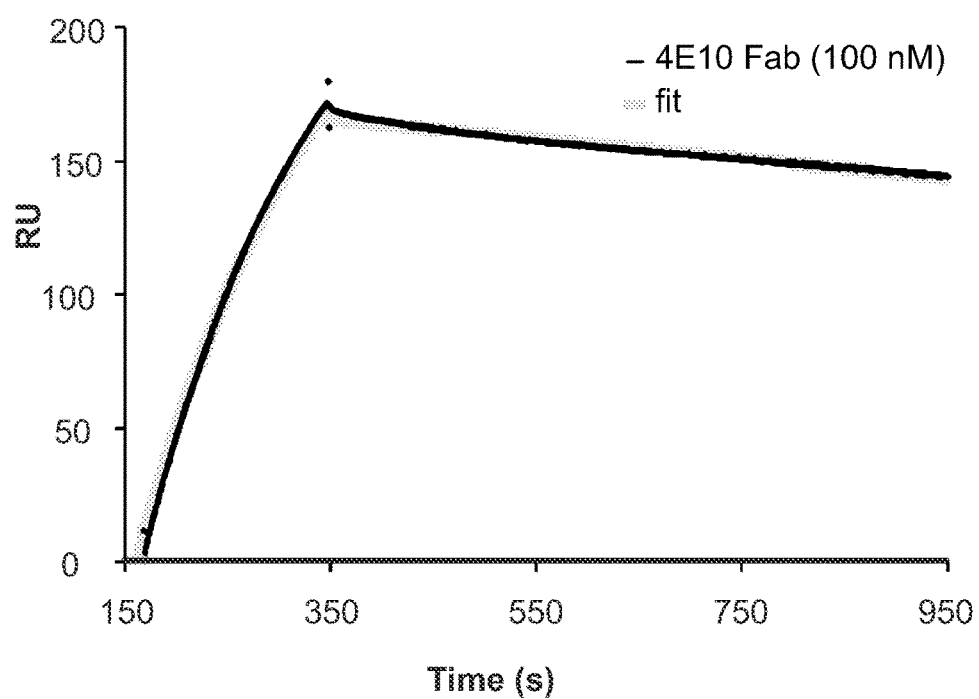
Figure 7E:
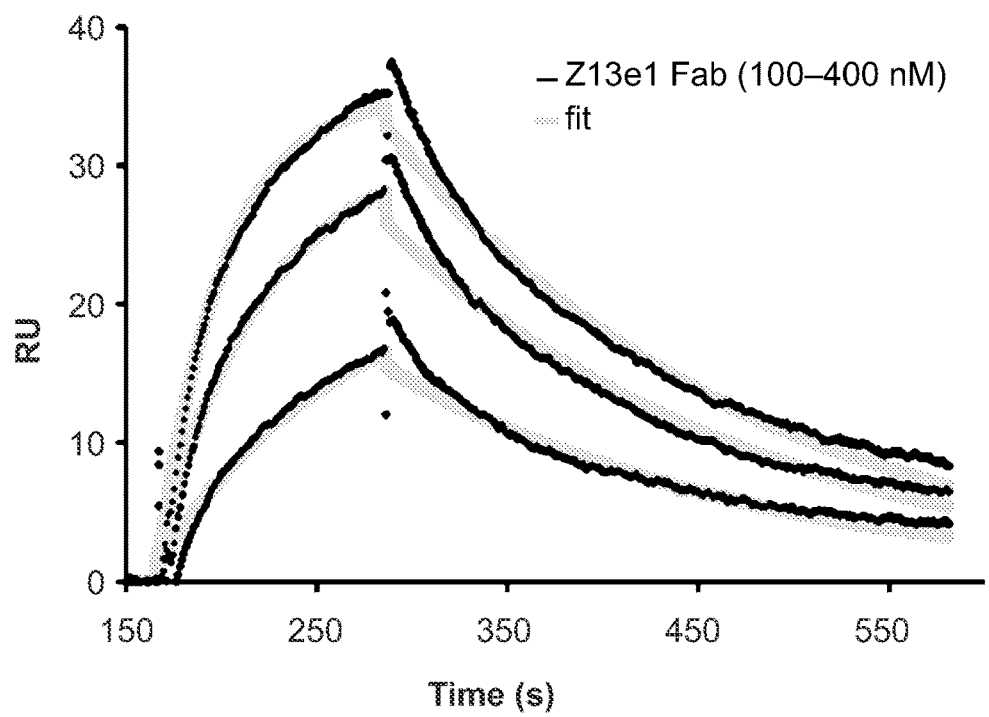
Figure 7F:
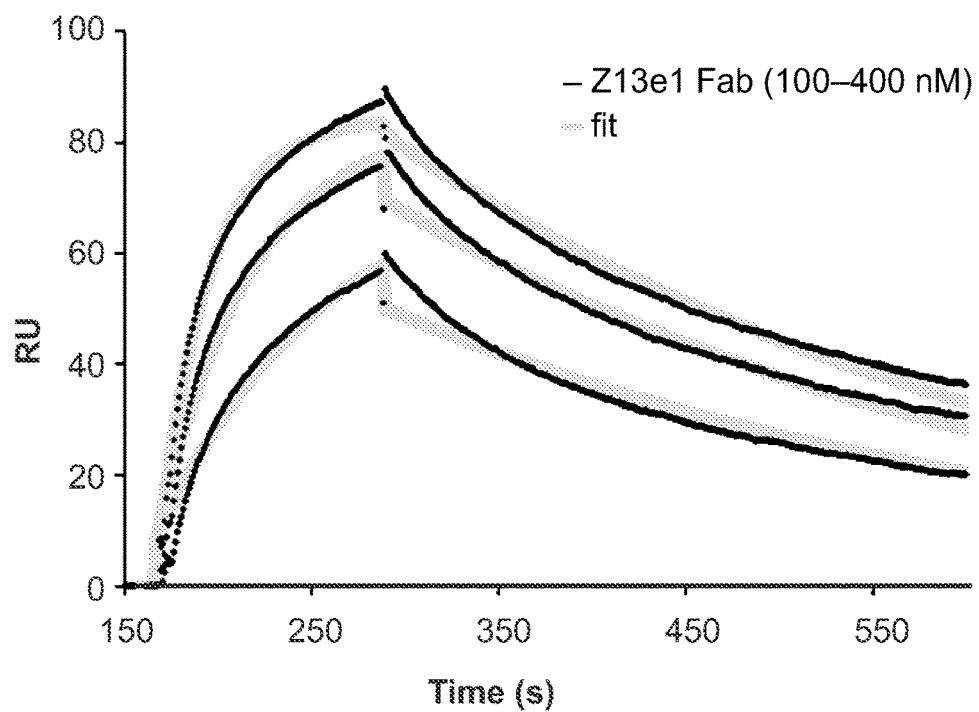

Homogeneous preparations of trimeric HIV-1 envelope protein, derived from a clade A isolate 92UG037.8, have been produced to mimic its pre-fusion (gp140), pre-hairpin intermediate (gp41-inter) and post-fusion (gp41-post) conformations (FIG. 1 and Frey et al., Supra). It was demonstrated that the different conformational states of gp41 exhibit markedly different antigenic characteristics. In particular, two MPER-directed neutralizing antibodies, 2F5 and 4E10, inhibit HIV-1 infection by targeting the pre-hairpin intermediate state of gp41 (Frey et al., Supra; Alam et al. (2009) *Proc. Natl. Acad. Sci. USA* 106:20234). To define the conformational state recognized by anti-gp41 cluster II antibodies, their reactivity to gp140, gp41-inter and gp41-post was tested. Gp41-inter was designed to capture gp41 in the extended, pre-hairpin intermediate conformation with the following sequence: (HR2)-linker-(HR1-CC loop-HR2-MPER)-(trimerization foldon tag) (FIG. 1). This construct can be pictured as the pre-hairpin intermediate captured by a covalently linked HR2 peptide, such as T20. When gp41-inter chains trimerize, the N-terminal HR2 segments (T20) form a six-helix bundle with the HR1 segments, while the C-terminal HR2 segments, constrained by the foldon tag, will be unable to form a six-helix bundle. Thus, the two copies of HR2 in gp41-inter are in distinct conformations: the N-terminal HR2 in the six-helix, post-fusion state and the C-terminal HR2 mimics the pre-hairpin intermediate. Using gp41-inter as a reagent to analyze antibodies directed against HR2, such as cluster II mAbs, would complicate data interpretation. Accordingly, a modified gp41-inter was designed in which the entire six-helix bundle (the segment HR2-linker-HR1) was replaced with a trimeric GCN4-derived coiled-coil to generate GCN4-gp41-inter (FIG. 1 and Harbury et al. (1994) *Nature* 371:80). The heptad repeat of GCN4 needed to be in the same register as the HR1 region of gp41 to avoid any structural distortion. GCN4-gp41-inter was expressed in *E. coli* and refolded in vitro following the same protocol we developed for gp41-inter (Frey et al., Supra). As expected, purified GCN4-gp41-inter is also a monodisperse trimer and stable after several rounds of gel-filtration chromatography (FIG. 6).

To confirm that replacement of the six-helix bundle with GCN4 did not alter antigenic properties of gp41-inter, binding experiments were performed using surface plasmon resonance (SPR) to assess reactivity of GCN4-gp41-inter to three MPER-directed mAbs 2F5, 4E10 and Z13e1. As shown in FIG. 7 and Table 1, both gp41-inter and GCN4-gp41-inter proteins show the same kinetic profile for binding to the antibodies, indicating that the conformation of MPER is identical in the two constructs. Note that Z13e1, the least potent neutralizing antibody among the three, dissociated from gp41 much more rapidly that did 2F5 and 4E10. Without intending to be bound by scientific theory, this observation is consistent with a slow dissociation rate of antibody-gp41 complex being critical for the neutralizing activity of MPER-directed antibodies (Alam et al., Supra). The interactions of gp41 with the three antibodies fit well to the 1:1 Langmuir binding model (FIG. 7). Moreover, both gp41-inter and GCN4-gp41-inter formed tight complexes with cluster I antibodies, such as 240-D and 246-D (Xu et al., Supra), which could be purified by gel filtration chromatography, indicating that substitution of the six-helix bundle with GCN4 did not introduce any structural distortion. It was concluded that GCN4-gp41-inter was trapped in the same fusion-intermediate conformation as was gp41-inter.

TABLE 1

Binding rate constants derived from SPR analysis.

| Immobilized ligand | Flowing analyte | ka (1/Ms) | kd (1/s) | Kd (M) |
|---|---|---|---|---|
| gp41-inter | 2F5 Fab | 4.57E5 | 1.90E−4 | 4.15E−10 |
| GCN4-gp41-inter | 2F5 Fab | 4.98E5 | 1.58E−4 | 3.17E−10 |
| gp41-inter | 4E10 Fab | 2.66E4 | 2.35E−4 | 8.85E−9 |
| GCN4-gp41-inter | 4E10 Fab | 4.88E4 | 2.37E−4 | 4.86E−9 |
| gp41-inter | Z13e1 Fab | 5.60E4 | 5.48E−3 | 9.77E−8 |
| GCN4-gp41-inter | Z13e1 Fab | 8.50E4 | 2.89E−3 | 3.40E−8 |
| gp41-post | 1281 Fab | 1.88E6 | 2.08E−3 | 1.11E−9 |
| gp41-inter | 1281 Fab | 9.66E5 | 2.76E−3 | 2.86E−9 |

Example II

The Post-Fusion Conformation of gp41 was Recognized by Cluster II Antibodies

Figures 1, 9:
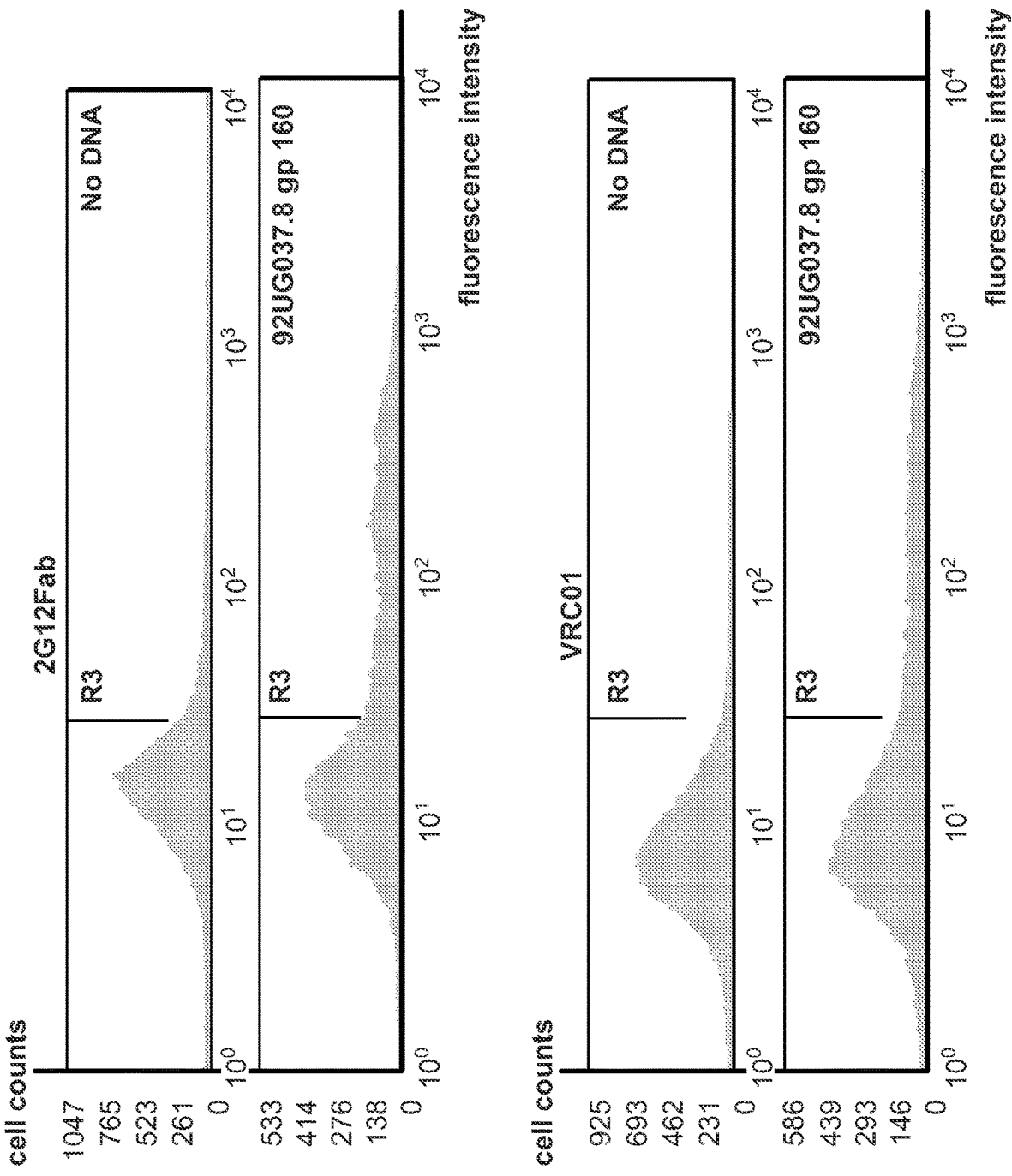
Figures 2, 9:
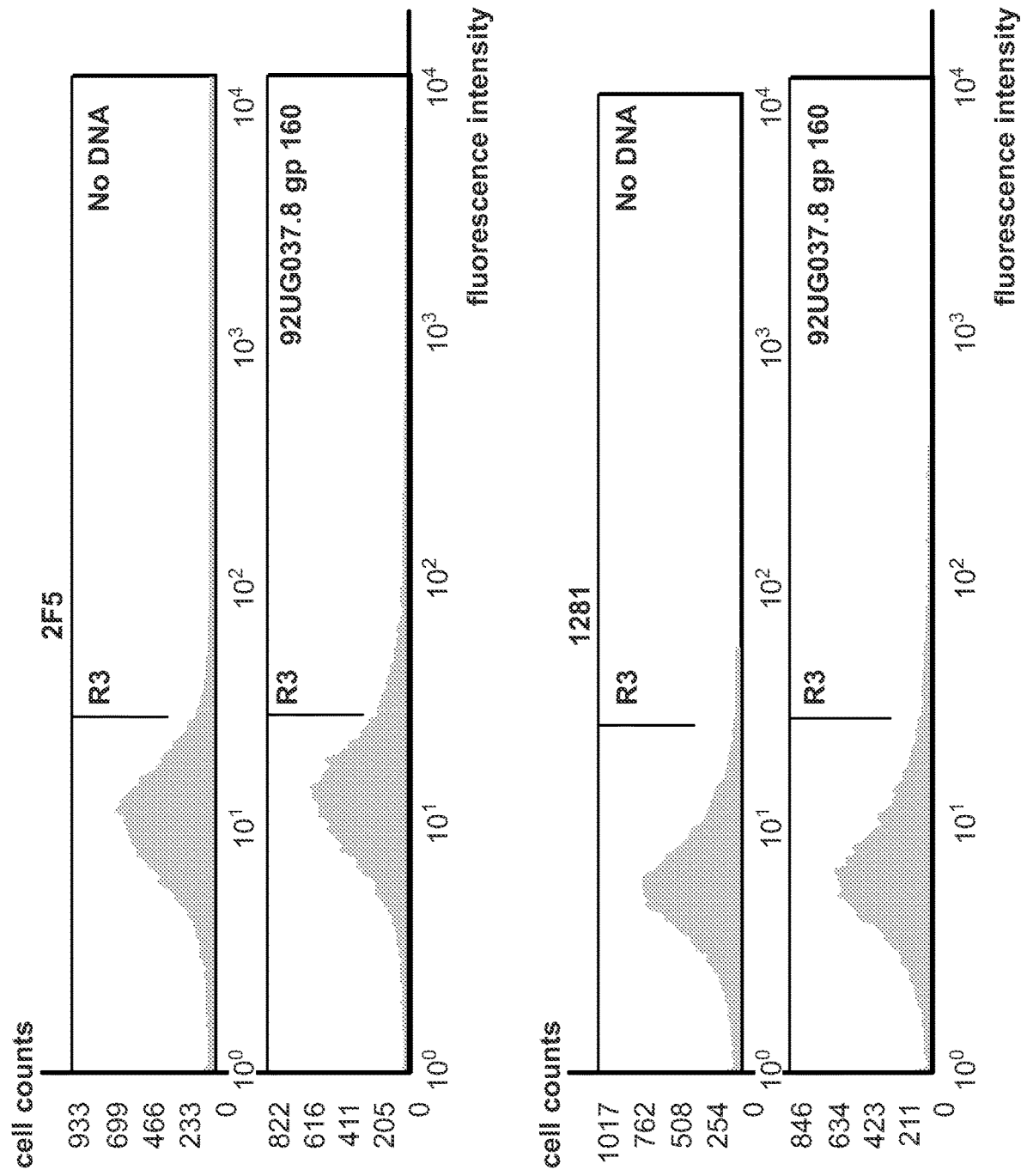
FIGS. 2A-2E graphically depict that anti-HIV-1 gp41 cluster II antibodies preferentially bind gp41 in its post-fusion conformation. Human anti-gp41 cluster II mAbs 1281, 98-6D, 126-7D, 167D and 1379 were analyzed by a surface plasmon resonance (SPR) assay for binding to HIV-1 gp41 constructs: gp140 (sensorgrams in black); GCN4-gp41-inter (blue); and gp41-post (red). GCN4-gp41-inter or gp41-post were immobilized on CM5 chips; gp140 was captured on a Ni-NTA chip. Each IgG at 50 nM was passed over each surface individually. Data with the antibodies immobilized on a Protein A chip are shown in FIG. 8.
Figures 3, 9:
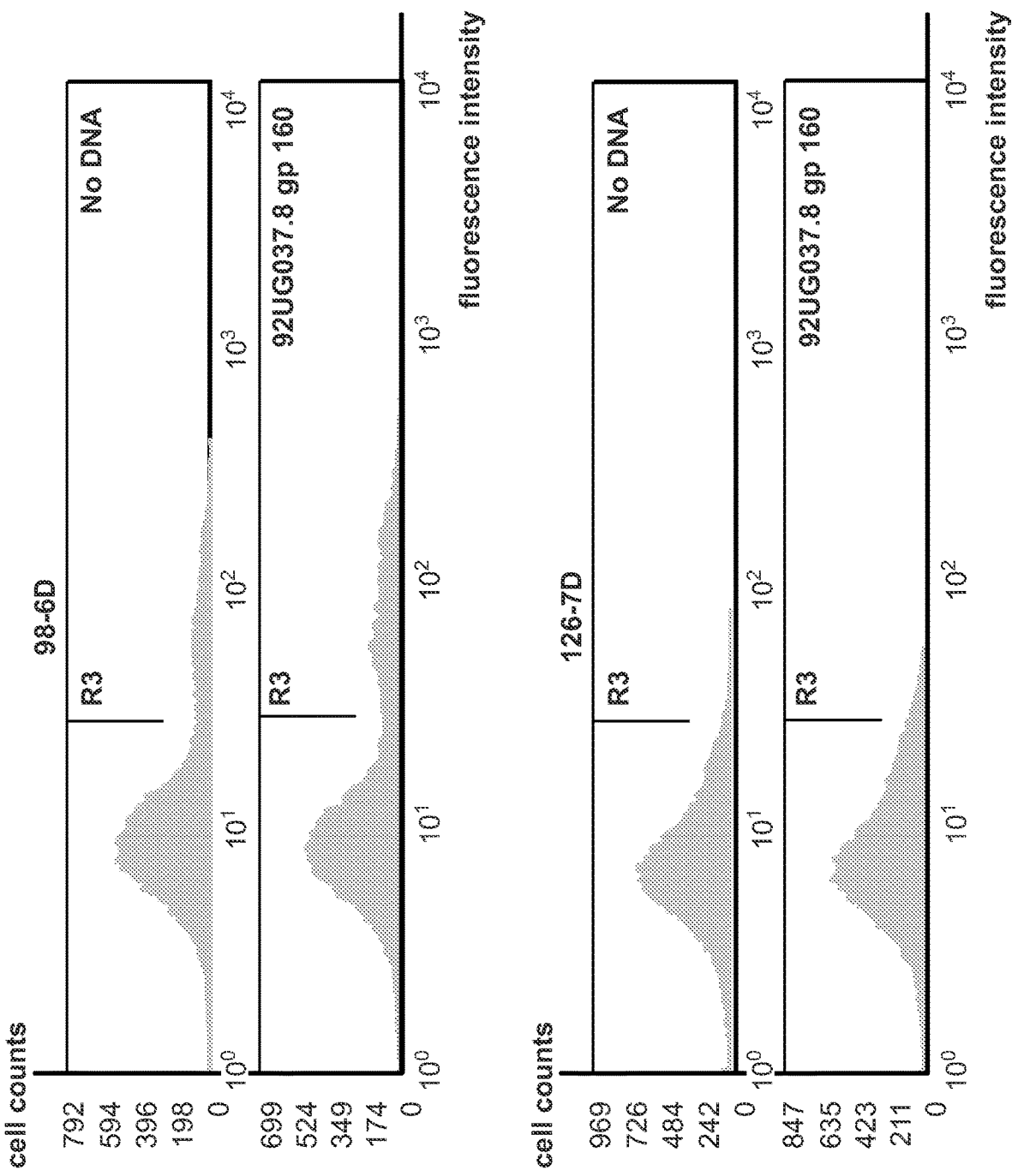

To assess binding specificity of cluster II antibodies, a panel of five human mAbs was chosen, including 98-6, 126-6, 167-D, 1281, and 1379 (Xu et al., Supra; Gorny (1989), Supra; Gorny (2000) *Virology*, Supra), and tested their reactivity to gp140, GCN4-gp41-inter and gp41-post by SPR. All the antibodies have been shown to bind a full-length recombinant gp41 and oligomeric gp140, as well as a six-helix bundle formed by HR1 and HR2 peptides using ELISA; 98-6 is the only one that reacts with an HR2 peptide alone (Gorny (2000) *Virology*, Supra; Gorny (2000) *J. Virol.*, Supra). As depicted in FIGS. 2 and 8, all the antibodies showed tight binding to the post-fusion conformation of gp41 with extremely fast on-rates, in agreement with the previous findings (Gorny (2000) *J. Virol.*, Supra), indicating that the six-helix bundle presents the optimal conformation recognized by these antibodies. In contrast, none of the antibodies showed any binding to GCN4-gp41-inter, which does contain the cluster II epitopes (residues 644-663), indicating the residues in gp41 critical for interacting with cluster II antibodies are either buried or not correctly configured for antibody recognition in the pre-hairpin intermediate state. In particular, mAb 98-6, capable of forming a complex with an unconstrained and flexible HR2 peptide, did not show any detectable binding to GCN4-gp41-inter, further confirming that gp41-inter presents a unique conformation that is incompatible with recognition by the non-neutralizing cluster II antibodies. The stringently characterized gp140 trimer showed only weak binding to four of these mAbs and no binding at all to mAb 1379 (FIGS. 2 and 8). Moreover, all the cluster II antibodies showed barely detectable binding to the same envelope trimer expressed on 293T cell surfaces, just as 2F5, which does not recognize the native, pre-fusion conformation of gp41 (FIG. 9). Taken together, the non-neutralizing, anti-HIV-1 gp41 cluster II antibodies only recognize the post-fusion conformational state of gp41, which is distinct from the fusion-intermediate conformation targeted by the MPER-directed broadly neutralizing antibodies.

Example III

Interaction of gp41-Post with the Monovalent Fab Fragment Derived from mAb 1281

Figure 3A:
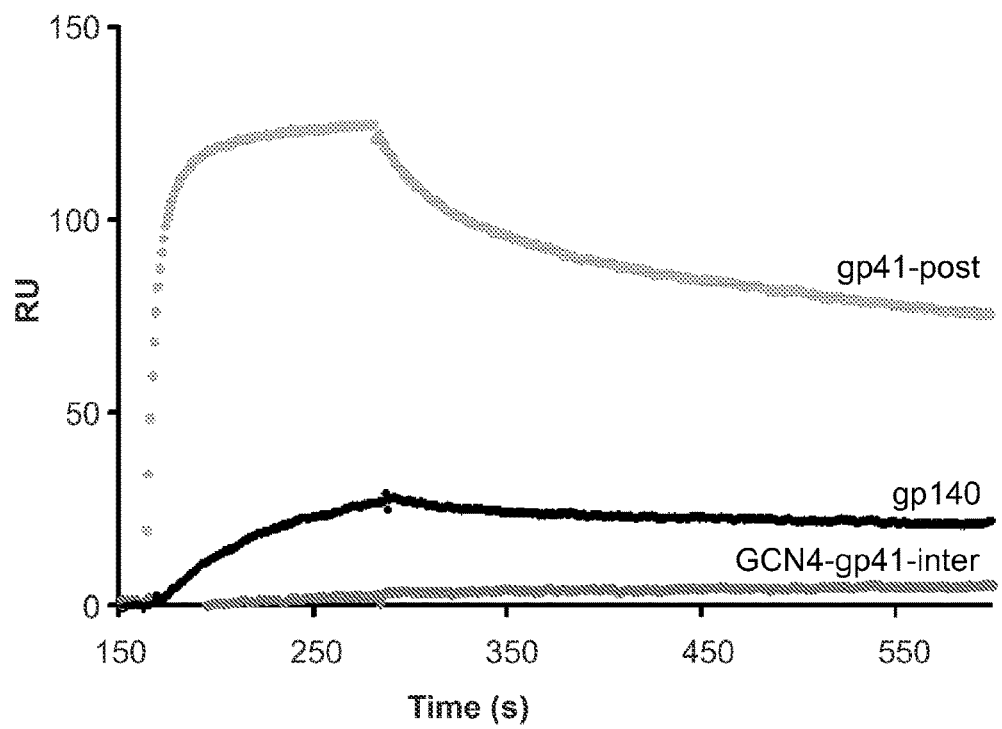
FIGS. 3A-3D graphically depict an analysis of interactions of 1281 Fab with various gp41 constructs. Fab fragment derived from mAb 1281 was tested by SPR for binding to gp41 constructs. (A) The recorded sensorgram for gp41-post is in red, gp140 in black and GCN4-gp41-inter in blue. (B) To confirm no detectable binding of 1281 Fab to GCN4-gp41-inter, solutions of 1281 Fab at various concentrations were flowed over the GCN4-gp41-inter surface. The sensorgrams are shown in various colors. In C and D, 1281 Fab at various concentrations was passed over the surfaces immobilized with gp41-post, and gp41-inter containing the six-helix bundle, respectively. Binding kinetics were evaluated using a 1:1 Langmuir binding model and binding constants are summarized in Table 1. The sensorgrams are shown in black and the fits in green. All injections were carried out in duplicate and gave essentially identical results. Only one of the duplicates is shown.
Figure 3B:
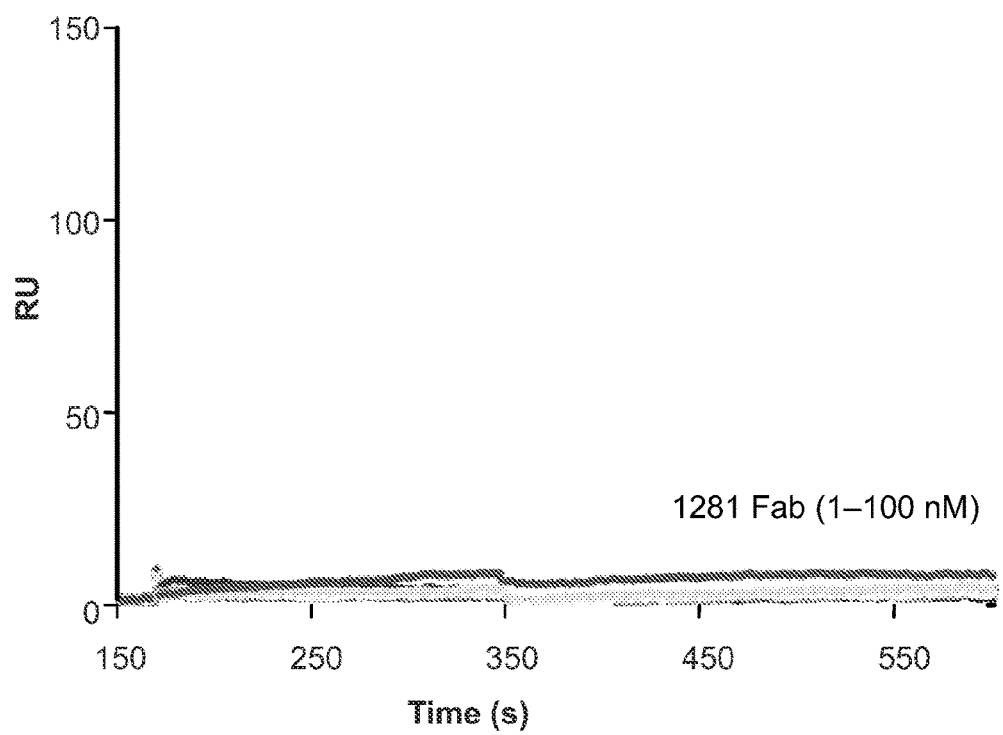
Figure 3C:
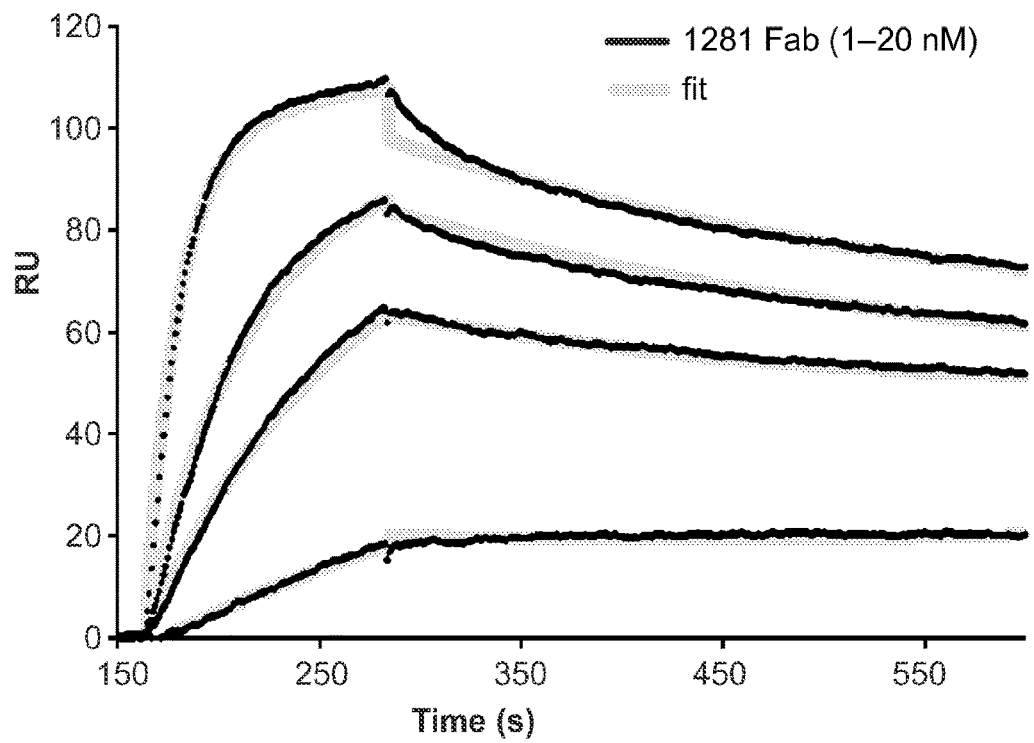
Figure 3D:
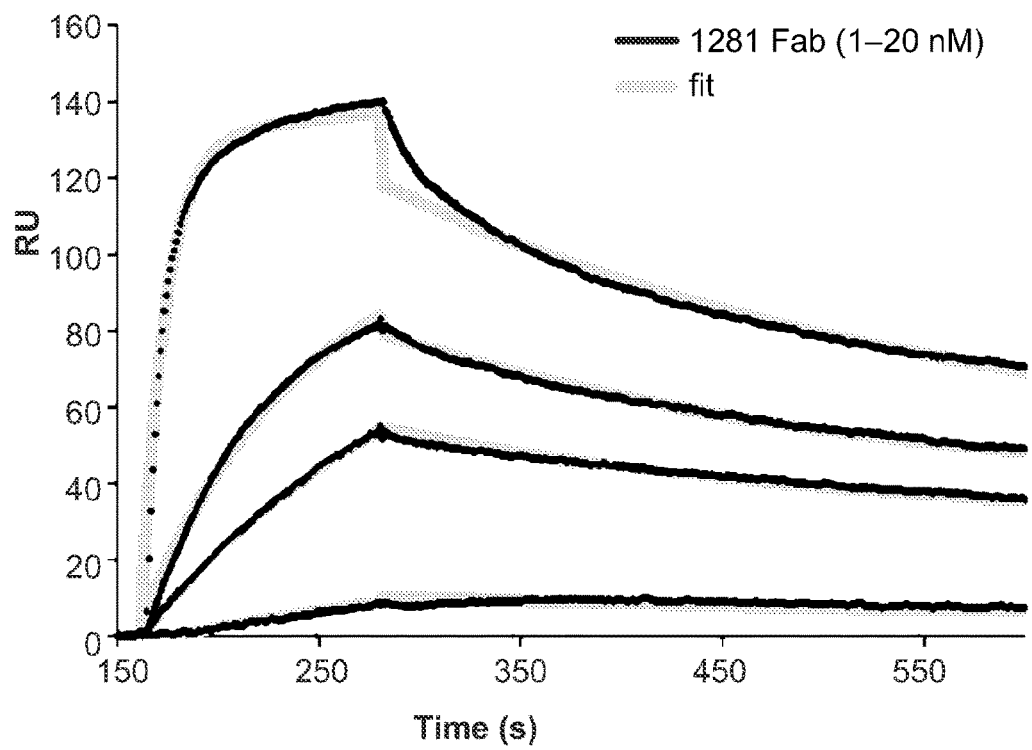

Although bivalent IgG is the physiologically relevant form, intrinsic affinity of its antigen-combining site to target antigens could be masked by avidity effects. To gain further insights into how cluster II antibodies interact with gp41 in its post-fusion conformation, mAb 1281 was chosen as a representative, and the Fab fragment was produced to eliminate avidity effects. As depicted in FIG. 3A, the 1281 Fab showed the same pattern for binding to the envelope proteins: high affinity to gp41-post, weak affinity to gp140 and no binding to GCN4-gp41-inter, fully consistent with the results using the intact IgG. Additionally, the Fab failed to interact with GCN4-gp41-inter in a wide range of concentrations (1-100 nM; FIG. 3B), further confirming the notion that HR2 adopts a completely different conformation in the pre-hairpin intermediate from the six-helix bundle conformation. It was predicted that gp41-inter with the N-terminal HR2 folding back on the HR1 to form a six-helix bundle would bind the 1281 Fab the same way as does gp41-post. Shown in FIGS. 3C and 3D, the kinetic properties of the Fab binding to gp41-inter and gp41-post were almost identical. Note that the kinetic characteristics of 1281 Fab binding to gp41-post were not that different from those of Z13e1 binding to gp41-inter, indicating that affinity of an antibody to gp41 alone is not an indicator of its antiviral activity.

Example IV

Crystal Structure of the Complex of Gp41-Post and the 1281 Fab Fragment

To obtain a structural definition of the cluster II epitopes, the crystal structure of the complex of gp41-post and 1281 Fab was determined at 3.3 Å resolution. Crystals of the 1281 Fab-gp41-post complex diffracted to 3.3 Å resolution and belonged to space group R3, with one Fab and one gp41 monomer per crystallographic asymmetric unit. The structure was determined by molecular replacement using HIV-1 gp41 monomer (pdb:1AIK; Chan et al., Supra) and a library of Fab coordinates as search models (Aoki et al. (2009) *Science* 324:1444). Searches for gp41 and Fab yielded convincing solutions. The constant region of 1281 Fab shared 100% sequence identity with that of the search model, and thus the two should have the same structure. However, density for the constant region remained poor throughout the rebuilding and refinement process (FIGS. 10A and 10B), indicating there was some packing disorder in this domain. The variable region together with gp41 could form a complete lattice in the absence of the constant domain, which may therefore have more than one orientation in the crystal (FIG. 10C). Complementarity determining regions (CDRs) of both heavy- and light-chains of 1281 were rebuilt iteratively, and the final model was refined with an $R_{work}$ of 26.1% and an $R_{free}$ of 28.9% (Table 2).

TABLE 2

Data collection and refinement statistics. Values in parentheses are for the highest-resolution shell.

|  | 1281 Fab-gp41-post |
|---|---|
| Data collection | |
| Space group | R3 |
| Cell dimensions | |
| a, b, c (Å) | 115.83, 115.83, 119.54 |
| α, β, γ (°) | 90, 90, 120 |
| Resolution (Å) | 33.4-3.30 (3.39-3.30)* |
| $R_{sym}$ or $R_{merge}$ | 8.7 (42.5) |
| I/σI | 16.5 (2.3) |
| Completeness (%) | 99.5 (99.8) |
| Redundancy | 3.2 (3.2) |

TABLE 2-continued

Data collection and refinement statistics. Values in parentheses are for the highest-resolution shell.

|  | 1281 Fab-gp41-post |
|---|---|
| Refinement | |
| Resolution (Å) | 33.4-3.30 (3.39-3.30) |
| No. reflections | 8,478 (640) |
| $R_{work}/R_{free}$ | 26.1(37.8)/28.9 (43.1) |
| No. atoms | |
| Protein | 3,771 |
| B-factors | |
| Protein | 130.6 |
| R.m.s. deviations | |
| Bond lengths (Å) | 0.005 |
| Bond angles (°) | 0.743 |

Figure 4A:
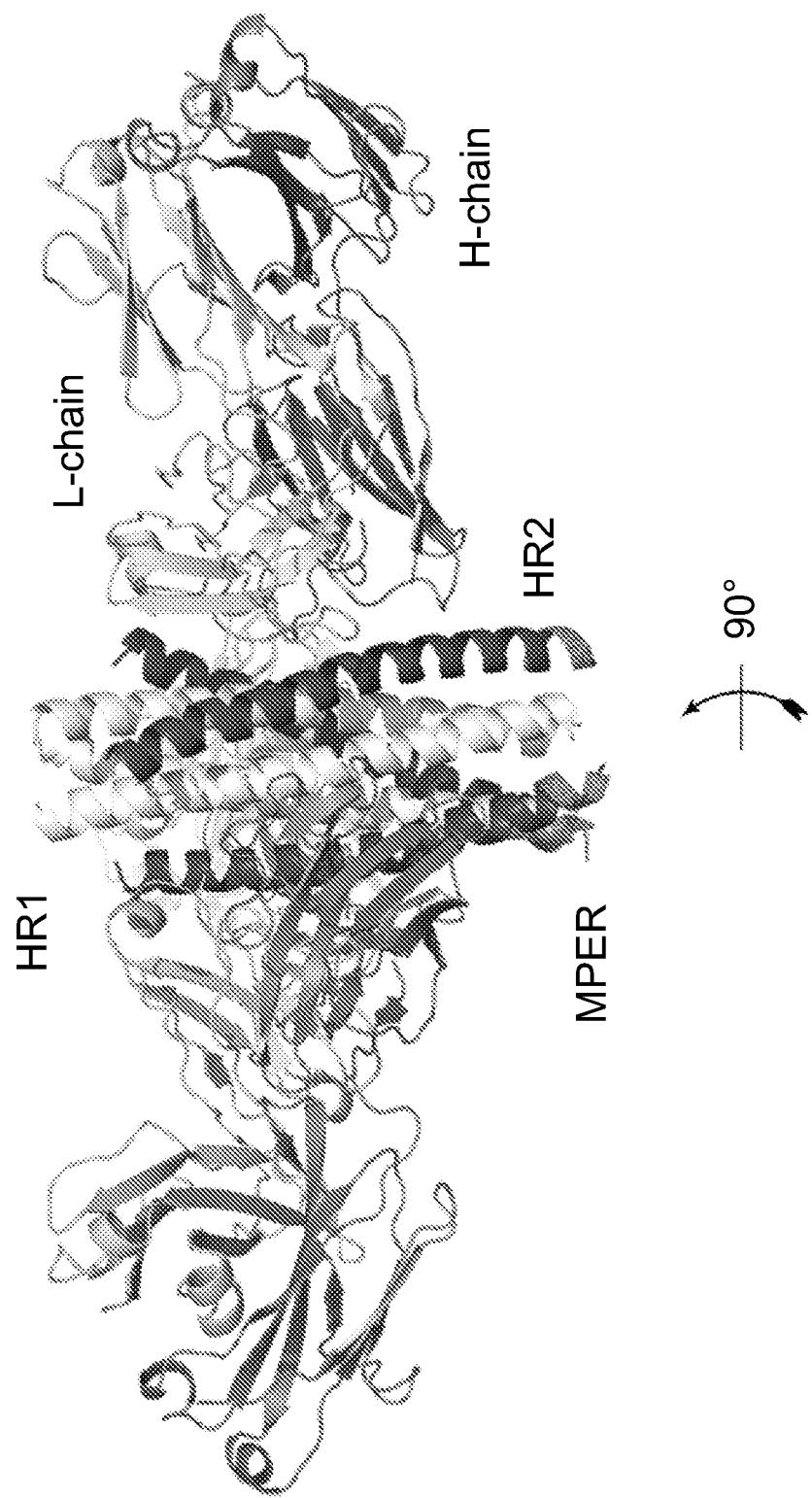
FIGS. 4A-4B schematically depict the crystal structure of the complex of gp41-post and the Fab fragment of cluster II antibody 1281. Side (A) and top (B) views of the overall structure of the post-fusion conformation of HIV-1 gp41 in complex with the Fab derived from an anti-gp41 cluster II mAb 1281 are shown in ribbon representation. The heavy chain of the antibody is in dark green and the light chain in light green; HR1 of gp41 in yellow, HR2 in blue and the part of MPER in red. The Fab primarily grips HR2, but also makes direct contacts with HR1 by CDR loops from both the heavy- and light-chains, indicating the six-helix bundle conformation of gp41 is critical for 1281 binding. The MPER part in red contains the 2F5 epitope (residues 663-669), which is α-helical in the post-fusion conformation.
Figure 4B:
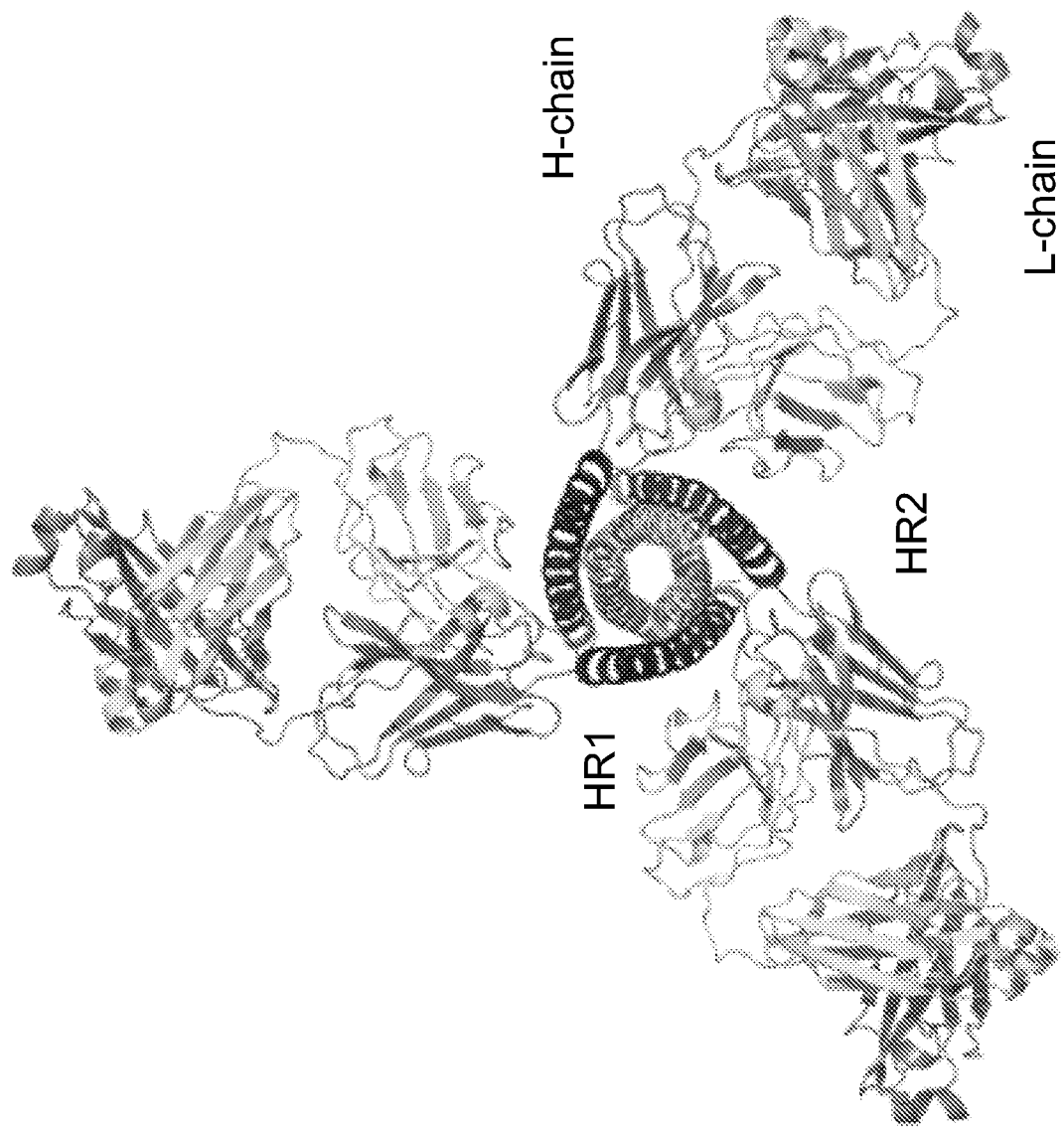
Figure 5A:
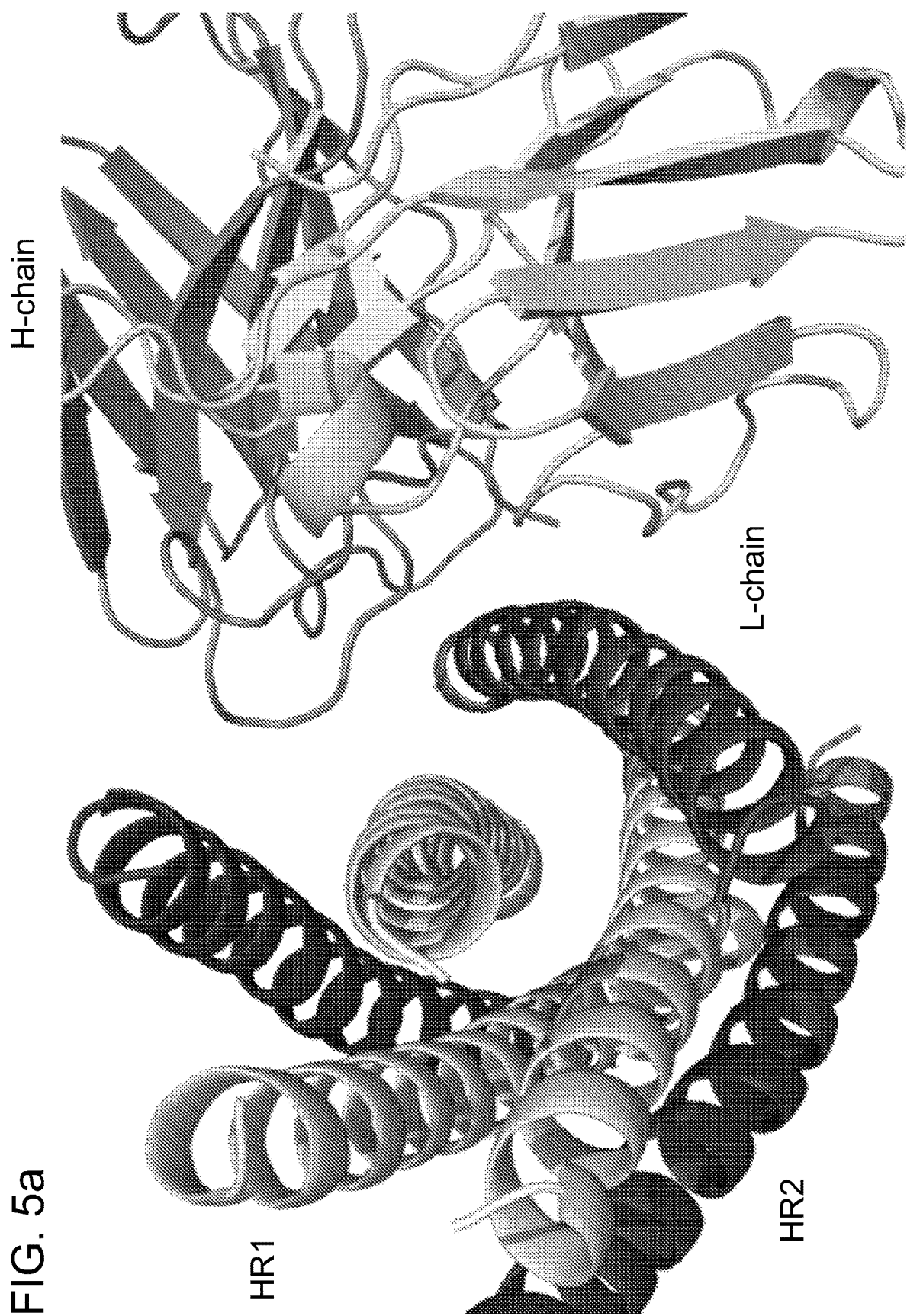
FIGS. 5A-5B schematically depict a close-up of major contacts between gp41 and 1281 Fab. Gp41 and 1281 Fab are both shown in ribbon diagram in A; gp41 in surface representation and the Fab in ribbon diagram in B. The heavy chain of the antibody is in dark green and the light chain in light green; HR1 of gp41 in yellow, HR2 in blue and the part of MPER in red; surface-exposed residues in HR2 are labeled in white. The CDR H1 and L2 loops of the antibody contact the HR2 helix in gp41-post; the CDR H3 reaches out and interacts with both the HR1 and HR2 helices. The footprint of the antibody covers residues 643-661, consistent with the previous epitope-mapping data (Xu et al., Infra; Gorny et al. (2000) *J. Virol.*, Infra; Yuan et al. (2009) *AIDS Res. Hum. Retroviruses* 25:319). The 2F5 in red is spatially close to the cluster II epitope.
Figure 5B:
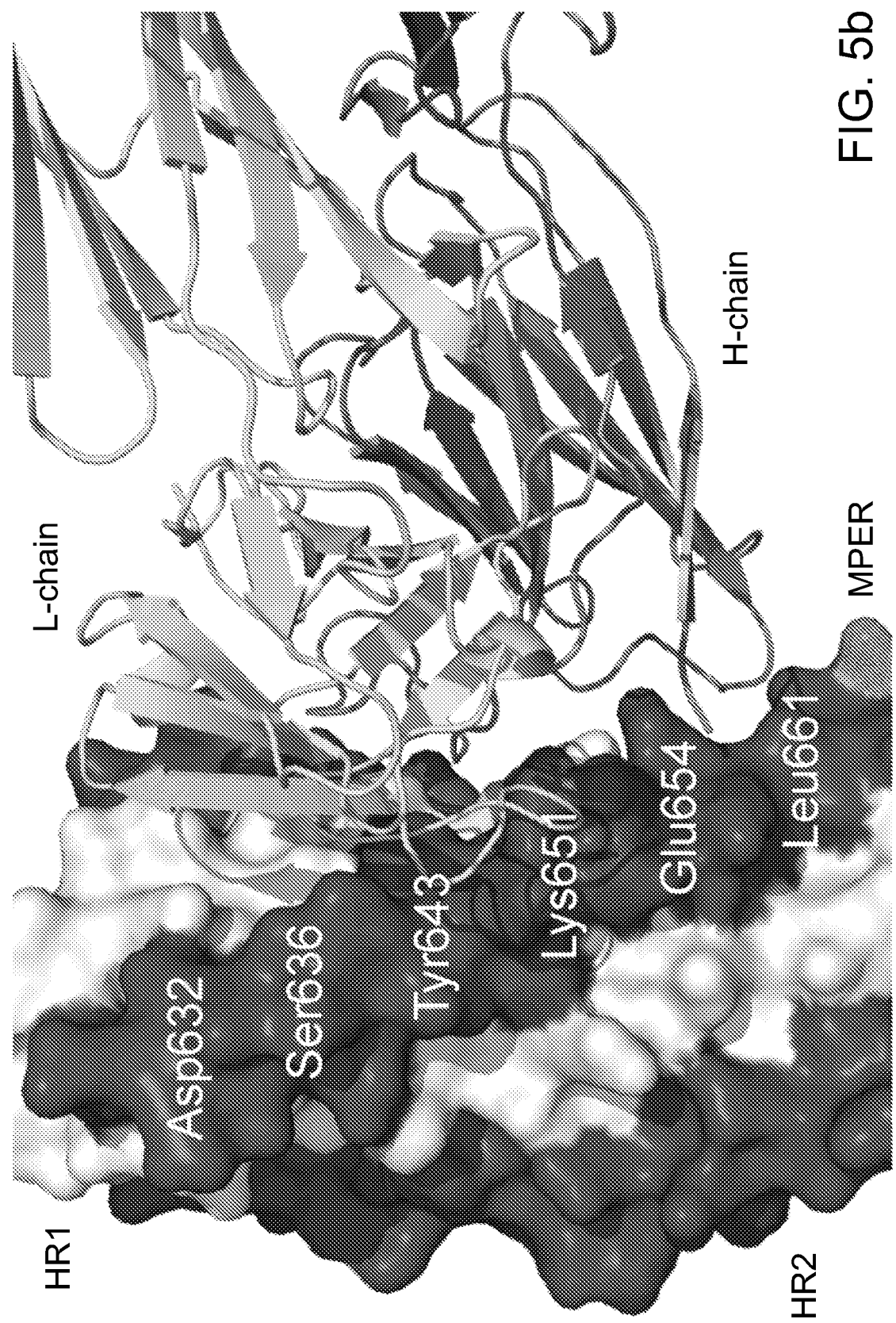
Figures 4, 9:
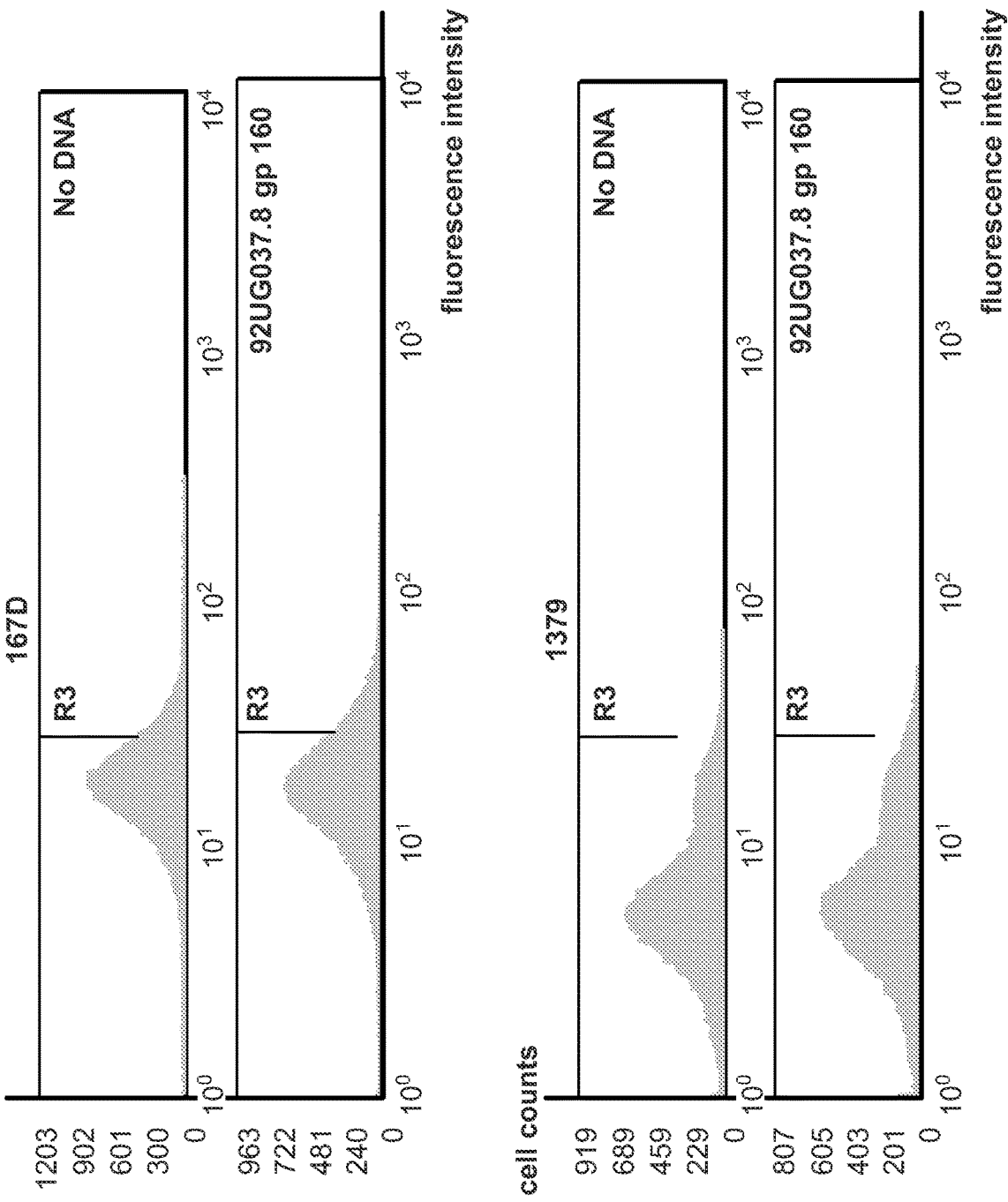

As expected, gp41-post derived from the clade A isolate 92UG037.8 formed a six-helix bundle similar to the structures of gp41 determined for HIV-1 clade B isolates and SIV (simian immunodeficiency viruses) (Chan et al., Supra; Weissenhorn et al., Supra; Caffrey et al. (1998) *EMBO J.* 17:4572; Yang et al. (1999) *J. Struct. Biol.* 126:131). The 2F5 epitope in the MPER of gp41-post adopted an α-helical conformation (FIG. 4) distinct from that in the crystal structure of the 2F5-gp41 peptide complex, where the epitope stretched into an extended conformation with two overlapping type I β turns (Ofek et al. (2004) *J. Virol.* 78:10724). The CDR loops from both the heavy- and light-chains of 1281 Fab made extensive interactions with the six-helix bundle. The CDR H1 and L2 loops contacted the HR2 helix in gp41-post exclusively, while the CDR H3 interacted with both the HR1 and HR2 helices (FIG. 4). Two segments (residues 101-104 and 107-109) of CDR H3 packed against the residues 560-564 in HR1 (FIG. 5A). The footprint of the antibody covered residues 643-661 of HR2 (FIG. 5B), fully consistent with previous epitope-mapping data (Xu et al., Supra; Gorny et al. (2000) *J. Virol.*, Supra; Yuan et al., Supra). The observation that 1281 Fab made direct contacts with the HR1 helix is in agreement with the previous findings that most cluster II antibodies interact with the six-helix bundle of gp41, but not with HR1 or HR2 peptide alone (Gorny et al. (2000) *J. Virol.*, Supra). Binding of 1281 Fab did not induce any obvious structural rearrangements in gp41, as judged by comparison of gp41-post with the other six-helix bundle structures (Chan et al., Supra; Weissenhorn et al., Supra). The distance between the centers of the 2F5 and 1281 epitopes was approximately 30 Å, confirming their spatial closeness on gp41 (FIGS. 4A and 5B).

Example V

Discussion

Developing a safe and effective vaccine that durably blocks HIV-1 infection is one of the highest priorities for global health. Conventional strategies based on empirical approaches have failed to provide adequate protection against HIV-1 infection in clinical trials (Pitisuttithum et al. (2006) *J. Infect. Dis.* 194:1661; Rerks-Ngarm et al. (2009) *New Engl. J. Med.* 361:2209). Innovative approaches are urgently needed. The HIV-1 envelope glycoprotein has evolved to undergo large structural rearrangements with very different conformational states during viral entry and each state exhibits distinct antigenic characteristics. Rational design of an effective envelope-based immunogen will likely require a deeper understanding of the structural correlates of envelope antigenicity and immunogenicity. The results described herein address the structural basis for the drastic differences between the MPER-directed antibodies and the cluster II antibodies in their ability to neutralize HIV-1 infection, despite their equivalently high affinity for HIV-1 gp41. The broadly neutralizing mAbs, 4E10 and 2F5, do not bind the pre-fusion form of gp41, but rather target only the pre-hairpin intermediate conformation (Frey et al., Supra). Gp41-inter, a gp41 design to mimic the pre-hairpin intermediate, was instrumental in that study. 4E10 and 2F5 bind almost irreversibly to gp41-inter, while their complexes with the soluble peptide epitopes dissociate much more rapidly (Id.), consistent with the notion that the very slow dissociation rate of the antibody-gp41 complex may be critical for targeting a fusion-intermediate, as dissociation could allow gp41 to proceed toward fusion. Moreover, addition of gp41-inter could efficiently block neutralization by 4E10 even when the antibody was pre-incubated with the virus (Alam et al., Supra), while the 4E10 epitope peptide was ineffective under the same setting, indicating that gp41-inter is in a conformation relevant to both membrane fusion and antibody neutralization. To examine conformational specificity of the cluster II mAbs, it was necessary to modify the original gp41-inter design by replacing the post-fusion component with an unrelated trimeric GCN4 (FIG. 1; Frey et al., Supra). It is demonstrated herein that anti-HIV-1 gp41 cluster II antibodies, which recognize a segment adjacent to the neutralizing epitopes in the MPER, showed high affinity only to gp41 in the post-fusion conformation. These antibodies are ineffective in preventing HIV-1 infection as they target a late step in the viral entry process, when membrane fusion is likely to be complete. Without intending to be bound by scientific theory, the stable, post-fusion conformation of gp41 likely serves as a decoy to help HIV-1 evade the immune system and induce ineffective antibody responses in infected patients. Rational design of gp41-based immunogens would require strategies to constrain gp41 and prevent it from folding into the six-helix bundle conformation.

Neutralizing antibodies against gp41 are rare, while gp41-specific non-neutralizing antibodies are often quite abundant (Xu et al., Supra). Cluster I antibodies directed at the C-C loop are not neutralizing, either because these epitopes are not readily accessible on the functional envelope trimer or because antibody binding to the C-C loop does not impede the envelope function (Hioe et al., Supra; Nyambi et al. (2000) *J. Virol.* 74:7096; Schulke et al. (2002) *J. Virol.* 76:7760). The reason why cluster II antibodies are non-neutralizing has been puzzling, however, especially, since their epitopes are near the broadly neutralizing epitopes in the MPER. Previous studies on the neutralization mechanism by MPER-directed mAbs show that 4E10 and 2F5 target the gp41 pre-hairpin intermediate (Frey et al., Supra; Alam et al., Supra). Furthermore, the ability of these antibodies to interact with HIV-1 membrane is critical for them to capture their MPER target presented in the transient intermediate state (Muñoz-Barroso et al. (1998) *J. Cell Biol.* 140:315; Steger and Root (2006) *J. Biol. Chem.* 281:25813). Without intending to be bound by scientific theory, it appears that neutralizing activity for an anti-gp41 antibody correlates with its capacity to bind viral membrane and gp41 in the fusion-intermediate conformation. Some cluster II mAbs, including 126-6, 167-D and 1281, can also interact with membrane lipids. In addition, the cluster II epitopes are more membrane-distal than the MPER, and these mAbs would need a much longer hydrophobic CDR loop to bind both gp41 and the membrane simultaneously. Thus, membrane-binding properties are unlikely to be the reason why the cluster II mAbs are not neutralizing. The results presented herein clearly demonstrate that the post-fusion conformation of gp41 is the high-affinity target of the cluster II antibodies. The only two opportunities when this conformational state of gp41 is accessible to antibodies during viral entry are either when gp120 dissociates prematurely (gp120 shedding) to leave nonfunctional gp41 "stumps" on the surface of virion (Moore et al. (2006) *J. Virol.* 80:2515), or when membrane fusion is complete. In both cases, binding by cluster II mAbs would not obstruct the function of gp41 and thus would have no impact on HIV-1 entry.

Cluster II antibodies could mediate HIV-1 specific antibody-dependent cellular cytotoxicity (ADCC) and other Fc-mediated antiviral activities (Holl et al., Supra; Alsmadi and Tilley (1998) *J. Virol.* 72:286; Tyler et al. (1990) *J. Immunol.* 145:3276; Forthal et al. (1995) *AIDS Res Hum Retroviruses* 11:1095). The data presented herein indicate that these antibodies only bind with high affinity to the triggered form of gp41 on the surface of virion, not the native envelope spikes. For any given HIV-1 envelope, ADCC that targets the cluster II epitopes would have to depend on how much gp120 sheds spontaneously and how many nonfunctional gp41 stumps are present on the viral membrane surface. Thus, cluster II mAb-mediated ADCC would be more effective against isolates which shed gp120 readily, while those with much more stable $(gp120\text{-}gp41)_3$ complex would be more resistant.

Cluster II epitopes are very immunogenic in vivo (Xu et al., Supra) and could help HIV-1 evade the immune system by triggering production of non-neutralizing antibody responses. A recent study to clone anti-HIV antibodies against HIV-1 gp41 from the memory B-cell compartment of HIV-1 infected individuals has shown that unique B-cell clones targeting cluster II epitopes account for 49% of all anti-gp41-reactive B cells (Pietzsch et al. (2010) *J. Virol.* 84:5032). Without intending to be bound by scientific theory, the crystal structure of 1281 Fab in complex of gp41-post demonstrates that the antibody makes direct contacts with both HR1 and HR2, indicating that the six-helix bundle is likely the immunogen that induces this type of antibody responses in HIV-1 infected patients. The gp120-depleted gp41 stumps observed on the surface of virions, which do interact with cluster II antibodies (Moore et al., Supra), are, without intending to be bound by scientific theory, likely in the triggered, six helix bundle form and may be the major source of gp41 immunogens responsible for this type of antibody responses. HIV-1 may thereby exploit the envelope stability as one of immune evasion tactics to distract the immune system from the native, functional trimers.

HIV-1 envelope-based immunogens often induce high ELISA-titer antibody responses with limited neutralizing activity or breadth. Most envelope immunogens containing gp41 are not rigorously characterized, particularly, in their conformational homogeneity. For example, HIV-1 gp140 preparations are often a mixture of monomers, dimers, trimers and aggregates, and it is difficult to discern what conformation each of these species represents and whether they are physiologically relevant. Gp41 could adopt the most stable, post-fusion conformation in some of these irrelevant forms and expose immunodominant, non-neutralizing epitopes, such as those recognized by the cluster II antibodies. These preparations could lead to misinterpretation of the antigenic and immunogenic properties of the envelope protein, and hence misguide the effort for immunogen design. Another important and understudied aspect of protein-based immunogen design is the potential impact that adjuvant formulation may have on immunogen structure. For instance, emulsions using oil-based adjuvants could potentially disrupt protein structural integrity and trigger conformational changes in gp41. Empirical approaches to develop gp41-based immunogens that overlook these structural details of immunogens might primarily induce non-neutralizing antibody responses. For a genuinely rational immunogen design, steps must be taken to prevent gp41 from folding into the post-fusion conformation.

Example VI

Materials and Methods

Coordinates and structure factors have been deposited in Protein Data Bank with accession code 3P30

Expression and Refolding of gp41 Proteins

Expression and purification of HIV-1 92UG037.8 gp140 and gp41-post were carried out as described (Frey et al., Supra), except that gp140 was produced in 293T cells. GCN4-gp41-inter had the following sequence: MQIEDKIEEILSKIYHIENEIARIKKLIGEQQLLGIWGCSGKLICTTNVPWNSSWSNKSEREIWENMTWLQWDKEISNYTHI IYELIEESQKQQEKNEQELLELDKWANLWNWFDISNWLWYIKSRGGSGGYIP EAPRDGQAYVRKDGEWVLLSTFL (SEQ ID NO:1) and was cloned into a pET-21a vector (Novagen). Following a protocol published previously (Id.), gp41-inter and GCN4-gp41-inter were expressed in *E. coli* as inclusion bodies, which were solubilized in 25 mM Tris pH 8.0 and 8 M urea. Gp41 proteins were then purified by a Q-Sepharose column under denaturing conditions using a column buffer containing 25 mM Tris pH 8.0 and 8 M urea, and eluted with a linear gradient of 0-1 M NaCl in the same buffer. The fractions containing gp41-inter or GCN4-gp41-inter were pooled. The protein was refolded a rapid-dilution protocol as described (Id.), and further purified by gel-filtration chromatography on a prep-grade Superdex 200 (GE Healthcare) in 25 mM Tris-HCl, pH 7.5 and 150 mM NaCl. Purified protein was concentrated and stored at −80° C.

Transfection and Flow Cytometry

Transfection of 293T cell with HIV-1 envelope constructs was carried out as described (Ferrer et al. (1999) *Nat. Struct. Biol.* 6:953). Transfected 293T cells were detached from plates using PBS containing 1% (w/v) BSA, followed by immediate addition of complete medium containing 10% FBS, and then washed with ice-cold PBS containing 1% BSA. $10^6$ cells per ml were incubated for 1 hour at 4° C. with anti-HIV-1 envelope monoclonal antibodies at 50 µg ml$^{-1}$, washed by PBS and then stained by a phycoerythrin-conjugated goat anti-human secondary antibody (Jackson ImmunoResearch) in PBS containing 1% BSA. Labeled cells were then washed with cold PBS with 1% BSA analyzed immediately using a MoFlo Legacy Cell Sorter and Summit Software v4.3 (Beckman Counter, Brea, Calif.).

Antibody and Fab Production

Human anti-HIV-1 gp41 cluster II monoclonal antibodies, 98-6, 126-6, 167-D, 1281 and 1379, were produced as described (Xu et al., Supra; Gorny et al. (1989), Supra; Gorny et al. (2000) *Virology*, Supra). Fab fragments of 2F5, 4E10 and Z13e1 were expressed in insect cells and purified by Gamma Bind Plus-Sepharose beads (GE Healthcare). Recombinant baculoviruses containing the heavy chain or the light chain of Fab were generated separately and mixed at a volume ratio of 1:1. Typically, 12 L of Sf9 cells were infected with recombinant baculoviruses at a multiplicity of infection of 2.5. The cell supernatants were harvested 72 hours post-infection by centrifugation, concentrated and loaded onto a Gamma Bind Plus-Sepharose column. Bound Fab was eluted by 100 mM glycine, pH 2.5 and further purified by gel filtration chromatography on a Superdex 200 (GE Healthcare). The Fab fragment of mAb 1281 was produced by papain (Sigma) digestion at 37° C. for 4 hours with an enzyme to antibody ratio of 1:1,000 by weight, and then purified by protein A affinity and gel-filtration chromatography.

SPR Binding Assays

All experiments were performed in duplicate with a Biacore 3000 instrument (Biacore Inc, Piscataway N.J.) at 20° C., with immobilization levels between 300 and 400 RU to avoid rebinding events. The experiments were run with a flow rate of 50 µl min$^{-1}$ with a 2 minute association phase and a 10 minute dissociation phase. HBS-EP (10 mM HEPES pH 7.4, 150 mM NaCl and 3 mM EDTA) was the running buffer for experiments using CM5 chips; and a buffer containing 10 mM HEPES pH 7.4, 150 mM NaCl, 50 µM EDTA and 0.005% (v/v) P20 for those using Ni-NTA chips.

Binding of 2F5, 4E10 or Z13e1 Fab to GCN4-41-inter and gp41-inter was performed as follows. GCN4-gp41-inter or gp41-inter was coupled to a CM5 chip at approximately 300-400 RU for 2F5 and 4E10 binding and at approximately 100 RU for Z13e1 binding using a standard amine coupling procedure. Sensorgrams were recorded by passing each Fab at various concentrations over the ligand surface. The surface was regenerated between each experiment by a single injection (3 seconds) of 35 mM NaOH and 1.3 M NaCl at a flow rate of 100 µl min$^{-1}$ 1281 Fab and cluster II IgGs binding to gp41-post and GCN4-gp41-inter were performed with gp41-post or GCN4-41-inter immobilized to a CM5 chip as described above. The chip surface was regenerated between each experiment using a single injection (3 seconds) of 35 mM NaOH and 1.3 M NaCl at a flow rate of 100 µl min$^{-1}$ Binding of 1281 Fab to the gp140 trimer was done by capturing the his-tagged gp140 on a Ni-NTA chip and 1281 Fab at various concentrations were passed over the chip surface. The surface was regenerated between each experiment with 10 mM HEPES, pH 8.3, 150 mM NaCl, 350 mM EDTA and 0.005% P20. To avoid potential artifacts introduced by protein immobilization to a CM5 chip, Protein A was first immobilized to a CM5 chip at approximately 1000 RU using the standard procedure. Each IgG was then captured to the Protein A surface at approximately 400 RU. Each of gp140, GCN4-gp41-inter or gp41-post at 50 nM was passed over each antibody surface individually. The surface was regenerated using 10 mM HCl. Binding kinetics were analyzed by BiaEvaluation software (Biacore) using a 1:1 Langmuir binding model. All injections were carried out in duplicate and gave essentially identical results.

Crystallization and Structure Determination

Crystals of the complex of gp41-post and 1281 Fab were obtained using hanging drop vapor diffusion method. Briefly, 1 µl of protein solution (15 mg ml$^{-1}$) was mixed with 1 µl of mother liquor (0.1 M Tris-HCl, 15% (w/v) PEG 4K) and allowed to equilibrate at 25° C. Crystals were flash frozen in liquid $N_2$ using 20% (v/v) glycerol in the mother liquor as a cryoprotectant. X-ray diffraction data were collected at 100° K at beamline 24-ID, Advanced Photon Source (Argonne National Laboratory, IL). The best crystals diffracted to a Bragg spacing of 3.3 Å with space group R3 (a=115.8, b=115.8, c=119.53). Initial phases were obtained by molecular replacement using the ectodomain of gp41 as a search model (Chan et al., Supra). The top solution of this search was fixed and a second search against a library of 244 antibody fragment structures was performed using MOL-REP and Phaser (Aoki et al., Supra; Vagin and Teplyakov (1997) *Acta. Crystallogr. D. Biol. Crystallogr.* 66:22; McCoy et al. (2007) *J. Appl. Crystallogr.* 40:658), yielding a single solution. The three-fold axis of the gp41 trimer coincided with the crystallographic three-fold, and there was one monomer of gp41 and one Fab in an asymmetric unit. Mild anisotropy in the data was observed and subsequently corrected using a diffraction anisotropy server prior to refinement (Strong et al. (2006) *Proc. Natl. Acad. Sci. USA* 103:8060). Electron density for the constant domain of the Fab fragment was poor. A complete lattice can form by the variable region of Fab and gp41 in absence of the constant domain, indicating that this domain may have more than one orientation in the lattice. The R factors were approximately 32% when the constant region was excluded for refinement. Model building was performed iteratively in O and Coot and refinement in Phenix and Refmac (Jones and Kjeldgaard (1997) *Methods Enzymol.* 277:173; Emsley et al. (2010) *Acta. Crystallogr. D. Biol. Crystallogr.* 66:486; Adams et al. (2010) *Acta. Crystallogr. D. Biol. Crystallogr.* 66, 213-21; Murshudov (1997) *Acta. Crystallogr. D. Biol. Crystallogr.* 53:240). The final model was refined with an $R_{work}$ of 26.1% and an $R_{free}$ of 28.9%. Analyzed by Procheck (Laskowski et al. (1993) *J. Appl. Cryst.* 26:283), 89.7% of residues are in most favored regions of the Ramachandran plot; 8.9%, in additional allowed regions; 1.3%, in generously allowed regions; and none in disallowed regions. All the structure figures were made in PyMOL (DeLano (2002) *The PyMOL User's Manual* (DeLano Scientific, San Carlos, Calif.)).

REFERENCE

Nelson et al. (2007) *J. Virol.* 81:4033

What is claimed:

1. An isolated, antigenic polypeptide comprising a pre-hairpin intermediate conformation of gp41 including:
    an oligomerization domain;
    a heptad repeat 2 motif; and
    a membrane-proximal external region,
    wherein the polypeptide lacks a heptad repeat 1 motif, and wherein the polypeptide elicits production of a broadly neutralizing antibody against HIV when injected into a subject.

2. The polypeptide of claim 1, further comprising a C-C loop domain.

3. The polypeptide of claim 1, wherein the oligomerization domain is a coiled coil domain.

4. The polypeptide of claim 1, wherein the polypeptide substantially fails to elicit production of weak or non-neutralizing antibodies when injected into a subject.

5. The polypeptide of claim 4, wherein the weak or non-neutralizing antibodies are cluster II antibodies.

6. An isolated, antigenic polypeptide comprising a pre-hairpin intermediate conformation of gp41 including:
an oligomerization domain;
a heptad repeat 2 motif; and
a membrane-proximal external region,
wherein the polypeptide elicits production of a broadly neutralizing antibody and substantially fails to elicit production of cluster II antibodies against HIV when injected into a subject.

7. An isolated, antigenic polypeptide comprising a pre-hairpin intermediate conformation of gp41 including:
an oligomerization domain;
a heptad repeat 2 motif; and
a membrane-proximal external region,
wherein the polypeptide lacks a post-fusion conformation of gp41 comprising a heptad repeat 1 motif and a heptad repeat 2 motif arranged as a bundle, and wherein the polypeptide elicits production of a broadly neutralizing antibody against HIV when injected into a subject.

8. An isolated, antigenic polypeptide comprising a pre-hairpin intermediate conformation of gp41 in the following order:
an oligomerization domain at the amino terminus of the polypeptide;
a C-C loop domain carboxy terminal to the oligomerization domain;
a heptad repeat 2 motif carboxy terminal to the C-C loop; and
a membrane-proximal external region at the carboxy terminus of the polypeptide.

9. The polypeptide of claim 8, wherein the polypeptide substantially fails to elicit production of weak or non-neutralizing antibodies when injected into a subject.

10. The polypeptide of claim 9, wherein the weak or non-neutralizing antibodies are cluster II antibodies.

11. The polypeptide of claim 8, wherein the polypeptide elicits production of a broadly neutralizing antibody when injected into a subject.

12. A method of inducing a neutralizing antibody response in a subject infected with a human immunodeficiency virus (HIV) comprising:
comprising administering to a subject infected with HIV an immunogenic composition comprising an isolated polypeptide comprising a pre-hairpin intermediate conformation of gp41 including an oligomerization domain, a heptad repeat 2 motif, and a membrane-proximal external region, and lacking a heptad repeat 1 domain;
wherein said polypeptide is capable of inducing a neutralizing antibody response against the HIV.

13. The method of claim 12, wherein gp41 is expressed in a single conformation in the subject.

14. The method of claim 12, wherein the polypeptide substantially fails to elicit production of cluster II antibodies in the subject.

15. A method of inhibiting HIV replication in a subject in need thereof comprising:
administering to an HIV-infected subject an immunogenic composition comprising an isolated polypeptide comprising a pre-hairpin intermediate conformation of an envelope glycoprotein including an oligomerization domain, a heptad repeat 2 motif, and a membrane-proximal external region, and lacking a heptad repeat 1 motif; and
inhibiting HIV replication.

16. The method of claim 15, wherein the HIV-mediated activity is viral spread.

17. The method of claim 15, wherein HIV titer in the HIV-infected subject is decreased.

18. A method of screening a compound that binds to an isolated, pre-hairpin intermediate conformation of gp41 comprising:
providing an isolated polypeptide including an oligomerization domain, a heptad repeat 2 motif, and a membrane-proximal external region, and lacking a heptad repeat 1 motif;
contacting the polypeptide with the compound; and
determining the ability of the compound to bind to the polypeptide, as compared to one or more controls.

19. A composition having an antigenic polypeptide comprising an isolated, pre-hairpin intermediate conformation of gp41 including an oligomerization domain, a heptad repeat 2 motif, and a membrane-proximal external region, and lacking a heptad repeat 1 motif, wherein the composition elicits production of a broadly neutralizing antibody against HIV when injected into a subject.

20. The method of claim 1, wherein the oligomerization domain is a GCN4 trimerization domain.

* * * * *

SEQUENCE LISTING

```
<160> NUMBER OF SEQ ID NOS: 1

<210> SEQ ID NO 1
<211> LENGTH: 157
<212> TYPE: PRT
<213> ORGANISM: Human immunodeficiency virus type 1

<400> SEQUENCE: 1

Met Gln Ile Glu Asp Lys Ile Glu Glu Ile Leu Ser Lys Ile Tyr His
1               5                   10                  15

Ile Glu Asn Glu Ile Ala Arg Ile Lys Lys Leu Ile Gly Glu Gln Gln
            20                  25                  30

Leu Leu Gly Ile Trp Gly Cys Ser Gly Lys Leu Ile Cys Thr Thr Asn
        35                  40                  45

Val Pro Trp Asn Ser Ser Trp Ser Asn Lys Ser Glu Arg Glu Ile Trp
    50                  55                  60

Glu Asn Met Thr Trp Leu Gln Trp Asp Lys Glu Ile Ser Asn Tyr Thr
65                  70                  75                  80

His Ile Ile Tyr Glu Leu Ile Glu Glu Ser Gln Lys Gln Gln Glu Lys
                85                  90                  95

Asn Glu Gln Glu Leu Leu Glu Leu Asp Lys Trp Ala Asn Leu Trp Asn
                100                 105                 110

Trp Phe Asp Ile Ser Asn Trp Leu Trp Tyr Ile Lys Ser Arg Gly Gly
            115                 120                 125

Ser Gly Gly Tyr Ile Pro Glu Ala Pro Arg Asp Gly Gln Ala Tyr Val
        130                 135                 140

Arg Lys Asp Gly Glu Trp Val Leu Leu Ser Thr Phe Leu
145                 150                 155
```